United States Patent [19]
Goodchild et al.

[11] Patent Number: 5,650,502
[45] Date of Patent: Jul. 22, 1997

[54] RIBOZYME ANALOGS HAVING RIGID NON-NUCLEOTIDIC LINKERS

[75] Inventors: John Goodchild, Westborough; Thomas E. Leonard, Marlboro, both of Mass.

[73] Assignee: Hybridon, Inc., Cambridge, Mass.

[21] Appl. No.: 336,526

[22] Filed: Nov. 9, 1994

[51] Int. Cl.$^6$ .......................... C07H 21/00; C07H 21/04; C07F 9/02; C12Q 1/68
[52] U.S. Cl. .......................... 536/23.2; 435/6; 435/91.31; 536/23.1; 536/24.5; 536/25.3; 558/70; 558/89
[58] Field of Search .......................... 435/91.31, 172.1, 435/199; 514/44; 536/23.1, 23.2, 24.3, 24.5, 25.3, 25.34; 558/70, 89

[56] References Cited

FOREIGN PATENT DOCUMENTS

| | | |
|---|---|---|
| 0 261 283 A1 | 3/1988 | European Pat. Off. . |
| WO93/15194 | 5/1993 | WIPO . |
| WO93/15187 | 5/1993 | WIPO . |
| WO94/13688 | 6/1994 | WIPO . |
| WO94/12633 | 9/1994 | WIPO . |
| WO94/10301 | 11/1994 | WIPO . |

OTHER PUBLICATIONS

Christoffersen et al. "Ribozymes as Human Therapeutic Agents" J. Medicinal Chem. 38(12): 2024–2036. Jun. 1995.
Goodchild (1992) *Nucleic Acids Research* 20:4607–4612.
Paolella et al. (1992) *EMBO Journal* 11:1913–1919.
Weast et al. *CRC Handbook of Chemistry and Physics*, 66th ed; 1985–1986, CRC Press, Inc. p. C–230.
Atkinson et al. *Oligonucleotide Synthesis: A Practical Approach* (Gait ed.) IRL Press, Ltd. Oxford (1984), pp. 35–81.
Haseloff et al. (1988) *Nature* 334:585–591.
Buzayan et al. (1990) *Nucleic Acids Res.* 18:4447–4451.
Dahm et al. (1990) *Biochem.* 72:819–23.
Goodchild (1990) *Bioconjugate Chem.* 2:165–187.
Odai et al. (1990) *FEBS Lett.* 267:150–152.
Perreault et al. (1990) *Nature* 344:565–567.
Ruffner et al. (1990) *Nucleic Acids Res.* 18:6025–6029.
Uhlmann et al. (1990) *Chem. Rev.* 90:534–583.
Goodchild et al. (1991) *Arch. Biochem. Biophys.* 284:386–391.
Koizumi et al. (1991) *Biochem.* 30:5145–5150.
Olsen et al. (1991) *Biochem.* 30:9735–9741.
Perreault et al. (1991) *Biochem.* 30:4020–4025.
Pieken et al. (1991) *Science* 253:314–317.
Agrawal et al. (1992) *Trends Biotech.* 10:152–158.
McCall et al. (1992) *Proc. Natl. Acad. Sci. (USA)* 89:5710–5714.
Beaucage et al. (1993) *Meth. Mol. Biol.* 20:33–61.
Benseler et al. (1993) *J. Am. Chem. Soc.* 115:8483–8484.
Damha et al. (1993) *Protocols for Oligonucleotides and Analogs; Synthesis and Properties* (Agrawal, ed.) Humana Press, Totawa, NJ, pp. 81–114.
Ma et al. (1993) *Biochem.* 32:1751–1758.
Ma et al. (1993) *Nucleic Acids Res.* 21:2585–2589.
Thomson et al. (1993) *Nucleic Acids Res.* 21:5600–5603.
Tuschl et al. (1993) *Proc. Natl. Acad. Sci. (USA)* 90:6991–6994.
Zon (1994) *Protocols for Oligonucleotides and Analogs* (Agrawal, ed.) Humana Press, Totawa, NJ, 20:165–189.

*Primary Examiner*—George C. Elliott
*Assistant Examiner*—Thomas G. Larson
*Attorney, Agent, or Firm*—Hale and Dorr LLP

[57] ABSTRACT

Disclosed are ribozyme analogs having the ability to endonucleolytically cleave a sequence of 3' to 5' linked ribonucleotides. The ribozyme analogs include a plurality of 3' to 5' covalently-linked nucleotides, and a rigid molecular linker having at least one non-nucleotidic molecule covalently linked to two of the nucleotides. Also disclosed are methods of preparing and utilizing the ribozyme analogs of the invention, and pharmaceutical formulations and kits containing such ribozyme analogs.

35 Claims, 9 Drawing Sheets

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: cDNA/RNA ( i i i ) HYPOTHETICAL: NO ( i v ) ANTI-SENSE: YES ( i x ) FEATURE:
                ( A ) NAME/KEY: positions 11-21 and 26- 33 are RNA ( x i ) SEQUENCE DESCRIPTION: SEQ ID NO:1:

TTTCCACACT CUGAUGAGGC CNNNNGGCCG AAAACTAAAA GGG          43

( 2 ) INFORMATION FOR SEQ ID NO:2:

( i ) SEQUENCE CHARACTERISTICS:
                ( A ) LENGTH: 34 base pairs
                ( B ) TYPE: nucleic acid
                ( C ) STRANDEDNESS: single
                ( D ) TOPOLOGY: linear ( i i ) MOLECULE TYPE: cDNA/RNA ( i i i ) HYPOTHETICAL: NO ( i v ) ANTI-SENSE: YES ( i x ) FEATURE:
                ( A ) NAME/KEY: positions 11-17 and 22- 25 are RNA ( x i ) SEQUENCE DESCRIPTION: SEQ ID NO:2:

TTTCCACACT CUGAUGANNN NGAAACTAAA AGGG          34

( 2 ) INFORMATION FOR SEQ ID NO:3:

( i ) SEQUENCE CHARACTERISTICS:
                ( A ) LENGTH: 28 base pairs
                ( B ) TYPE: nucleic acid
                ( C ) STRANDEDNESS: single
                ( D ) TOPOLOGY: linear ( i i ) MOLECULE TYPE: cDNA/RNA ( i i i ) HYPOTHETICAL: NO ( i v ) ANTI-SENSE: YES ( i x ) FEATURE:
                ( A ) NAME/KEY: positions 7-14 and 19- 23 are RNA ( x i ) SEQUENCE DESCRIPTION: SEQ ID NO:3:

CACACTCUGA UGAGNNNNCG AAACTAAA          28

( 2 ) INFORMATION FOR SEQ ID NO:4:

( i ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear ( i i ) MOLECULE TYPE: cDNA/RNA ( i i i ) HYPOTHETICAL: NO ( i v ) ANTI-SENSE: YES ( i x ) FEATURE:
                ( A ) NAME/KEY: positions 7-15 and 20- 25 are RNA ( x i ) SEQUENCE DESCRIPTION: SEQ ID NO:4:

CACACTCUGA UGAGGNNNNC CGAAACTAAA          30

( 2 ) INFORMATION FOR SEQ ID NO:5:

( i ) SEQUENCE CHARACTERISTICS:

(A) LENGTH: 33 base pairs
(B) TYPE: nucleic acid
(C) STRANDEDNESS: single
(D) TOPOLOGY: linear (ii) MOLECULE TYPE: cDNA/RNA (iii) HYPOTHETICAL: NO (iv) ANTI-SENSE: YES (ix) FEATURE:
(A) NAME/KEY: positions 7-16 and 21-27 are RNA (xi) SEQUENCE DESCRIPTION: SEQ ID NO:5:

CACACTCUGA UGAGGCNNNN GCCGAAAACT AAA　　　　33

(2) INFORMATION FOR SEQ ID NO:6:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: cDNA/RNA (iii) HYPOTHETICAL: NO (iv) ANTI-SENSE: YES (ix) FEATURE:
(A) NAME/KEY: positions 7-17 and 20-27 are RNA (xi) SEQUENCE DESCRIPTION: SEQ ID NO:6:

CACACTCUGA UGAGGCCNNG GCCGAAACTA AAA　　　　33

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:7:

CACTCUGAUG ANGAAACTAA　　　　20

(2) INFORMATION FOR SEQ ID NO:8:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:8:

CACTCUGAUG AGGNCCGAAA CTAA　　　　24

(2) INFORMATION FOR SEQ ID NO:9:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: cDNA/RNA ( i i i ) HYPOTHETICAL: NO ( i v ) ANTI-SENSE: YES ( x i ) SEQUENCE DESCRIPTION: SEQ ID NO:9:

CACTCUGAUG AGGCCNGGCC GAAACTAA                         28

( 2 ) INFORMATION FOR SEQ ID NO:10:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA/RNA ( i i i ) HYPOTHETICAL: NO ( i v ) ANTI-SENSE: YES ( x i ) SEQUENCE DESCRIPTION: SEQ ID NO:10:

CACACTCUGA UGAGNNNNNN CGAAACTAAA A                   31

( 2 ) INFORMATION FOR SEQ ID NO:11:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA/RNA ( i i i ) HYPOTHETICAL: NO ( i v ) ANTI-SENSE: YES ( x i ) SEQUENCE DESCRIPTION: SEQ ID NO:11:

CACACTCUGA UGAGGNNNNN NCCGAAACTA AAA                33

( 2 ) INFORMATION FOR SEQ ID NO:12:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA/RNA ( i i i ) HYPOTHETICAL: NO ( i v ) ANTI-SENSE: YES ( x i ) SEQUENCE DESCRIPTION: SEQ ID NO:12:

CACACTCUGA UGAGGCCNNN NNNGGCCGAA ACTAAAA            37

( 2 ) INFORMATION FOR SEQ ID NO:13:

( i ) SEQUENCE CHARACTERISTICS:
        ( A ) LENGTH: 47 base pairs
        ( B ) TYPE: nucleic acid ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: YES ( x i ) SEQUENCE DESCRIPTION: SEQ ID NO:13:

GGGAUUUUCC ACACUCUGAU GAGGCCGUUA GGCCGAAACU AAAAGUU    47

( 2 ) INFORMATION FOR SEQ ID NO:14:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: YES ( x i ) SEQUENCE DESCRIPTION: SEQ ID NO:14:

GGGAAAACAG ACCCUUUUAG UCAGUGUGGA AAAUC    35

( 2 ) INFORMATION FOR SEQ ID NO:15:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: YES ( x i ) SEQUENCE DESCRIPTION: SEQ ID NO:15:

TTTCCACACT CUGAUGAGGC CGUUAGGCCG AAACTAAAAG GG    42

( 2 ) INFORMATION FOR SEQ ID NO:16:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:16:

AGGGTCTGTT TTC    13

( 2 ) INFORMATION FOR SEQ ID NO:17:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: RNA (iii) HYPOTHETICAL: NO (iv) ANTI-SENSE: YES (xi) SEQUENCE DESCRIPTION: SEQ ID NO:17:

CACACUCUGA UGAGGCCGUU AGGCCGAAAC U   31

(2) INFORMATION FOR SEQ ID NO:18:

(i) SEQUENCE CHARACTERISTICS:
 (A) LENGTH: 34 base pairs
 (B) TYPE: nucleic acid
 (C) STRANDEDNESS: single
 (D) TOPOLOGY: linear (ii) MOLECULE TYPE: RNA (iii) HYPOTHETICAL: NO (iv) ANTI-SENSE: YES (xi) SEQUENCE DESCRIPTION: SEQ ID NO:18:

CACACUCUGA NGAGGCCGUU AGGCCGAAAC UAAA   34

(2) INFORMATION FOR SEQ ID NO:19:

(i) SEQUENCE CHARACTERISTICS:
 (A) LENGTH: 34 base pairs
 (B) TYPE: nucleic acid
 (C) STRANDEDNESS: single
 (D) TOPOLOGY: linear (ii) MOLECULE TYPE: RNA (iii) HYPOTHETICAL: NO (iv) ANTI-SENSE: YES (xi) SEQUENCE DESCRIPTION: SEQ ID NO:19:

AAUACUCUGA NGAGGCCGNN AGGCCGAAAC GCUC   34

(2) INFORMATION FOR SEQ ID NO:20:

(i) SEQUENCE CHARACTERISTICS:
 (A) LENGTH: 34 base pairs
 (B) TYPE: nucleic acid
 (C) STRANDEDNESS: single
 (D) TOPOLOGY: linear (ii) MOLECULE TYPE: RNA (iii) HYPOTHETICAL: NO (iv) ANTI-SENSE: YES (xi) SEQUENCE DESCRIPTION: SEQ ID NO:20:

AAUACUCUGA UGAGGCCGUU AGGCCGAAAC GCUC   34

RIBOZYME ANALOGS HAVING RIGID NON-NUCLEOTIDIC LINKERS

BACKGROUND OF THE INVENTION

This invention relates to the molecules with endonucleolytic activity and enhanced half-lives useful in the site-specific cleavage of RNA. This invention also relates to the control of gene expression through the degradation of mRNA.

Ribozymes are RNA molecules with catalytic activities including the ability to cleave at specific phosphodiester linkages in RNA molecules to which they have hybridized, such as mRNAs, RNA-containing substrates, and ribozymes, themselves.

Ribozymes may assume one of several physical structures, one of which is called a "hammerhead." A hammerhead ribozyme is composed of a catalytic core containing nine conserved bases, a double-stranded stem and loop structure (stem-loop II), and two regions complementary to the target RNA flanking regions the catalytic core. The flanking regions enable the ribozyme to bind to the target RNA specifically by forming double-stranded stems I and III. Cleavage occurs in cis (i.e., cleavage of the same RNA molecule that contains the hammerhead motif) or in trans (cleavage of an RNA substrate other than that containing the ribozyme) next to a specific ribonucleotide triplet by a transesterification reaction from a 3', 5'-phosphate diester to a 2', 3'-cyclic phosphate diester. It is currently believed that this catalytic activity requires the presence of specific, highly conserved sequences in the catalytic region of the ribozyme.

Although the endonucleolytic activity of ribozymes has been demonstrated in vitro, their use in vivo has been limited by their susceptibility to RNAses. Furthermore, the production of therapeutics such as ribozymes having greater than 30 or more nucleotides are more expensive and difficult to produce in great quantities. Thus, there is a need for smaller molecules with increased nuclease resistance that can be used to cleave RNA in vitro and in vivo, and to control gene expression for in vivo use.

In an effort to protect antisense oligonucleotides from degradative influences in vivo, various structural modifications have been made to these molecules, including the replacement of phosphodiester linkages with non-phosphodiester linkages, the substitution of various sugar groups and bases, the addition of end-capping groups, and the substitution or replacement of existing structures with the self-hybridizing termini (reviewed in Goodchild (1990) *Bioconjugate Chem.* 1:165–187; Agrawal et al. (1992) *Trends Biotechnol.* 10:152–158; WO 93/15194; WO 94/10301; WO 94/12633).

However, modifications which protect an RNA molecule from endonuclease digestion may also affect the catalytic activity of the ribozyme. For example, Perreault et al. (*Nature* (1990) 344:565–567) report that the replacement of ribonucleotides at various conserved positions within the ribozyme sequence with 2'-deoxynucleotides resulted in a 96% decrease of catalytic efficiency. Perreault et al. (*Biochem.* (1991) 30:4020–4025) and Dahn et al. (*Biochem.* (1990) 72:819–23) disclose that the replacement of various 2'-hydroxyl groups with hydrogen atoms reduced the catalytic activity of hammerhead ribozymes. Olsen et al. (*Biochem.* (1991) 30:9735–9741) report that replacing 2'-hydroxyl groups on all adenosine residues by either fluorine or hydrogen decreases the catalytic activity of a ribozyme. Odai et al. (*FEBS Lett.* (1990) 267:150–152) report that replacing the exocyclic amino group of a conserved guanosine residue in the core region with hydrogen reduced catalytic activity. Ruffner et al. (*Nucleic Acids Res.* (1990) 18:6025–6029) and Buzayan et al. (*Nucleic. Acids Res.* (1990) 18:4447–4451) disclose that replacing oxygen atoms by sulfur on various internucleotide phosphate residues reduces catalytic activity. Pieken et al. (*Science* (1991) 253:314–317) disclose that catalytic activity is reduced when various 2'-hydroxyl groups on adenosine residues are replaced with fluorine and when the 2'-hydroxyl groups on cytidine residues is replaced with amine groups.

Other groups have substituted nucleotides within the ribozyme with nucleotide analogs. For example, Usman et al. (WO 93/15187) designed chimeric polymers or "nucleozymes" with ribozyme-like catalytic activity having ribonucleotides or nucleic acid analogs (with modified sugar, phosphate, or base) at catalytically critical sites and nucleic acid analogs or deoxyribonucleotides at non-catalytically critical sites.

Recently, modifications such as a reduction in the length of the stem-loop II structure of the hammerhead ribozyme have been made in an effort to design a more stable molecule without reducing its catalytic activity. For example, Goodchild et al. (*Arch. Biochem. Biophys.* (1991) 284:386–391) replaced stem II and loop II with shorter nucleotide sequences. Tuschl et al. (*Proc. Natl. Acad. Sci. (USA)* (1993) 90:6991–6994) prepared hammerhead ribozymes with the stem II shortened to two base pairs, closed by a four base-pair loop. McCall et al. (*Proc. Natl. Acad. Sci. (USA)* 89:5710–5714) replaced the stem-loop with a few nucleotides that cannot form Watson-Crick base pairs between themselves, and/or substituted the stem-loop II and flanking arms with DNA, without reducing activity.

Modifications in ribozyme structure have also included the substitution or replacement of various non-core portions of the molecule with non-nucleotidic molecules. For example, Benseler et al. (*J. Am. Chem. Soc.* (1993) 115:8483–8484) disclosed hammerhead-like molecules in which two of the base pairs of stem II, and all four of the nucleotides of loop II were replaced with non-nucleoside linkers based on hexaethylene glycol, propanediol, bis(triethylene glycol) phosphate, tris(propanediol) bisphosphate, or bis(propanediol) phosphate. Ma et al. (*Biochem.* (1993) 32:1751–1758; *Nucleic Acids Res.* (1993) 21:2585–2589) replaced the six nucleotide loop of the TAR ribozyme hairpin with non-nucleotidic, ethylene glycol-related linkers. Thomson et al. (*Nucleic Acids Res.* (1993) 21:5600–5603) replaced loop II with linear, non-nucleotidic linkers of 13, 17, and 19 atoms in length.

However, nucleotides in neither the stem-loop region nor nonconserved regions of the catalytic core of the ribozyme have heretofore been replaced with more rigid, non-nucleotidic molecules. Non-nucleotide linkers or inserts with restricted rotation would give a less flexible molecule more in keeping with the requirements of an enzyme.

Thus, what is needed are molecules with improved nuclease resistance and endonucleolytic activity, and which can be quickly and cost-effectively prepared.

SUMMARY OF THE INVENTION

The present invention provides catalytic nucleotidic molecules or ribozyme analogs with increased nuclease resistance that are capable of endonucleolytically cleaving single-stranded RNA. These ribozyme analogs include a rigid, non-nucleotidic linker comprising at least one molecule or "unit" which has been substituted either into the stem-loop or the unconserved region of the catalytic core of the ribozyme.

It has been discovered that a rigid molecular linker can be formed of at least one non-nucleotidic molecule. It has also been discovered that replacement of some or all of the stem-loop II and the nonconserved region of the catalytic core of a ribozyme with at least one rigid, non-nucleotidic molecule can be accomplished without extinguishing the ability of the resulting ribozyme analog to endonucleolytically cleave single-stranded RNA. Although ribozymes with nucleotidic and non-nucleotidic substitutions have been prepared, none to date have been substituted with the rigid, non-nucleotidic molecules set forth in this application. Furthermore, substitution of the entire stem-loop II region has not been accomplished heretofore without eliminating the activity of the resulting ribozyme to endonucleolytically cleave single-stranded RNA.

These findings have been exploited to develop the present invention which, in one aspect, includes a rigid molecular linker. The linker contains at least one rigid non-nucleotidic molecule or "unit," which, in preferred embodiments, include cyclohexane diols, steroids, lupene diols, isosorbides, or combinations thereof.

The term "non-nucleotidic" is used herein to describe molecules or specific portions thereof which do not include nucleotides or nucleotide analogs. Accordingly, the term "nucleotidic" refers to nucleotide- or nucleotide analog-containing molecules or specific portions thereof.

For purposes of the invention described herein, the term "rigid" refers to the physical state of molecular structures having degrees of freedom of intramolecular rotation that are restricted in comparison with those of a simple linear chain.

In some embodiments of the invention, the linker includes at least two contiguously situated, covalently-linked non-nucleotidic molecules. In such embodiments the molecules of the linker are covalently linked via a phosphodiester, alkylphosphonate, phosphorothioate, phosphorodithioate, alkylphosphonothioate, phosphoramidate, phosphate ester, carbamate, carbonate, acetamidate, or carboxymethyl ester linkage, or by a combination thereof.

In some preferred embodiments, the linker includes 2 to 20 non-nucleotidic molecules. In other embodiments, the linker includes at least four covalently-linked cyclohexane diol units, such as a trans-1,2-cyclohexane diol, cis-1,2-cyclohexane diol, trans-1,3-cyclohexane diol, cis-1,3-cyclohexane diol, trans-1,4-cyclohexane diol, cis-1,4-cyclohexane diol, and combinations thereof. One specific linker of the invention consists of 4 cyclohexane diol units.

In another aspect of the invention, a method of preparing a non-nucleotidic molecular linker is provided. In this method, a plurality of rigid, non-nucleotidic molecules are covalently attached, via a linkage selected from the group consisting of a phosphodiester, phosphoramidate, alkyl phosphonate, phosphorothiate, phosphorodithioate, alkylphosphonothioate, phosphate ester, carbamate, carbonate, acetamidate, carboxymethyl ester, or combinations thereof. In one embodiment, a plurality of trans 1-O-(4,4'-dimethoxytrityl)-2-O-($\beta$-cyanoethyoxy-(N,N-diisopropylamine)] phosphino-1,2-cyclohexanediol units is prepared. A first of such units is covalently linked to a second of such units. Then a third of such units is covalently linked to the second of such units, and a fourth of such units is covalently linked to the third of such units, thereby forming the molecular linker.

Another aspect of the invention is a molecular linker prepared according to the method described immediately above.

In another aspect, the present invention provides a "ribozyme analog" or ribozyme-like RNA-containing molecules having an endonucleolytic activity and structure similar to a hammerhead ribozyme, but in contrast, having the rigid molecular linker described above substituted into, or replacing the entire stem-loop II region.

In one embodiment, a ribozyme analog of the invention has a nucleotidic stem-loop II region including the rigid, non-nucleotidic molecular linker, flanked by and covalently linked to a first nucleotidic core region and a second nucleotidic core region. The first and second nucleotidic core regions form a catalytic core. A first nucleotidic flanking region is linked to the first catalytic core, and a second nucleotidic flanking region is linked to the second catalytic core region.

The stem-loop II region of the ribozyme analog of the invention includes a plurality of 3' to 5' covalently-linked, self-hybridizing nucleotides and has a 3' terminus and a 5' terminus which are covalently linked to the rigid molecular linker.

As used herein, the term "self-hybridizing" refers to nucleotides in the stem region on the stem-loop II which are complementary to each other, and which form normal Watson-Crick base pairs. This stem region has two complementary nucleotidic strands which include at least one nucleotide on one stand and one nucleotide on the other strand which base pair together. In one non-limiting embodiment, the stem of the stem-loop has from 2 to 6 base-pairs.

The stem-loop II is covalently attached to a first and a second nucleotidic, single-stranded nucleotidic core region. Each nucleotidic core region includes a plurality of 3' to 5' covalently-linked nucleotides, and each has a 3' terminus and a 5' terminus. The 3' terminus of the first nucleotidic core region is linked to the 5' terminus of the stem-loop II, and the 5' terminus of the second nucleotidic core region is covalently linked to the 3' terminus of the stem-loop II.

The catalytic core region is flanked by first and second flanking regions. The first flanking region has at least a portion which is complementary to a first target region of a substrate RNA molecule, and the second flanking region has at least a portion which is complementary to a second target region of a substrate RNA molecule. At least four nucleotides in the first flanking region are complementary to at least four nucleotides in the first target region of the substrate RNA, and at least four nucleotides in the second flanking region are complementary to at least four nucleotides in the second target region of the substrate RNA. The first target region and the second target region are exclusive of each other.

As used herein, the term "complementary" refers to the ability of the flanking region to hybridize with a specific sequence of nucleotides in the normal Watson-Crick base-pairing fashion.

The terms "target RNA" and "substrate RNA" refers to the oligoribonucleotide composed of 3' to 5' covalently-linked ribonucleotides which the ribozyme analog recognizes and cleaves.

The 3' terminus of the first flanking region is covalently linked to the 5' terminus of the first nucleotidic core region, and the 5' terminus of the second flanking region is covalently linked to the 3' terminus of the second nucleotidic core region.

In some embodiments, the first and second flanking regions and the first and second nucleotidic core regions contain a plurality of nucleotides which are covalently linked by an internucleotide linkage selected from the group consisting of a phosphodiester, alkylphosphonate, phosphorothioate, phosphorodithioate, alkylphosphonothioate, phosphoramidate, phosphate ester, carbamate, carbonate, acetamidate, carboxymethyl ester linkage, or a combination of such linkages.

In preferred embodiments, the first and second flanking regions and the first and second nucleotidic core regions are composed of ribonucleotides, analogs of ribonucleotides, deoxyribonucleotides, analogs of deoxyribonucleotides, and combinations thereof.

As used herein, the term deoxyribonucleotide, ribonucleotide, or nucleotide "analog" is meant to encompass a nucleotide having a modified structure. Modifications include additions, reductions, or substitutions in any portion of the nucleotide include its sugar, base, or phosphate groups.

In some embodiments, the ribonucleotide or deoxyribonucleotide analogs are alkylphosphonates, phosphorothioates, phosphorodithioates, alkylphosphonothioates, phosphoramidates, phosphate esters, phosphate triesters, carbamates, carbonates, acetamidate, carboxymethyl esters, and combinations thereof. In one particular embodiment, at least one ribonucleotide analog in the ribozyme analog is a 2'-O-methyl ribonucleotide analog.

In another embodiment of the invention, a ribozyme analog is provided which includes a rigid molecular linker flanked by two nucleotidic core regions making up a catalytic core, and two flanking regions. The linker includes at least one non-nucleotidic molecule covalently linked to the two nucleotidic core regions. Each nucleotide core region includes a plurality of 3' to 5' covalently-linked nucleotides and each has 3' and 5' termini. Each flanking region includes at least four 3' to 5' covalently-linked nucleotides. The 5' terminus of the first nucleotidic core region is covalently linked to the 3' terminus of the first flanking region, and the 3' terminus of the second nucleotidic core region is covalently linked to the 5' terminus of the second flanking region. At least a portion of the first flanking region is complementary to a first target region on a substrate RNA molecule, and at least a portion of the second flanking region is complementary to a second target region on the same substrate RNA molecule.

Another aspect of the invention is a method of controlling the expression of a substrate RNA molecule. In this method, a ribozyme analog of the invention is provided and used to contact the RNA. By "provided" is meant to supply, make available, or prepare. The first flanking region of the ribozyme analog hybridizes to the first target region of the substrate RNA, the second flanking region hybridizes to the second target region of the substrate RNA, thereby enabling the ribozyme analog to cleave the substrate RNA. In this way, the expression of the substrate RNA, e.g., its ability to be translated into protein, is controlled.

In some embodiments of the method, the substrate RNA to be cleaved is also contacted with a facilitator oligonucleotide at the same time as it is contacted with the ribozyme analog. As used herein, a "facilitator oligonucleotide" encompasses oligonucleotides which are complementary and hybridizable to a sequence of ribonucleotides on the RNA substrate which is adjacent the first or second target regions targeted by either flanking regions of the ribozyme analog.

In another embodiment of the invention, a method of site-specifically cleaving a single-stranded, RNA-containing substrate is provided which includes providing a ribozyme analog of the invention and then contacting the RNA-containing substrate molecule with the ribozyme analog such that the first flanking region of the ribozyme analog hybridizes to the first target region of the substrate RNA, and the second flanking region of the ribozyme analog hybridizes to the second target region of the substrate RNA molecule thereby enabling the ribozyme analog to site-specifically cleave the RNA substrate.

As used herein, the term "site-specifically cleaving" refers to enzymatically cutting the phosphate backbone of the substrate RNA molecule before or after a particular sequence of ribonucleotides.

In some embodiments, the method further includes contacting the substrate RNA molecule with a facilitator oligonucleotide at the time it is contacted with the ribozyme analog.

Another aspect of the invention is a method of preparing the ribozyme analogs described herein. In this method, a first flanking region is formed by covalently linking together a plurality of nucleotides. This is accomplished by linking the 3' terminus of one nucleotide to the 5' end of another nucleotide, and so on. Then, the nucleotides of the first nucleotidic core region are covalently-linked, 3' to 5', one by one, to the 5' terminus of the first flanking region. The nucleotides of one strand of the double-stranded stem II are then covalently-linked, 3' to 5', to the 5' terminus of the first nucleotidic core region. At least one non-nucleotidic molecule forming the rigid molecular linker is then attached to the 5' terminus of the stem II region via a covalent linkage. In some embodiments, these covalent linkages are a phosphodiester, alkylphosphonate, phosphate ester, phosphorothioate, phosphorodithioate, alkylphosphonothioate, carbamate, carbonate, acetamidate, carboxymethyl ester, or phosphoramidate, linkage.

The second strand of the stem II is then built onto the unattached end of the linker. This is accomplished by linking the 3' terminus of a nucleotide to the non-nucleotidic molecule of the linker, followed by the covalent linkage of a plurality nucleotides, 3' to 5', one by one, to the nucleotide already bound to the linker, and then to each other, the 3' terminus of the nucleotide to be bound linked to the 5' terminus of the nucleotide already bound. Likewise, to the 3' end of the second strand of the stem II is covalently-linked a plurality of nucleotides making up the second nucleotidic core region, the 5' terminus of one nucleotide first being linked to the 3' terminus of the second strand of the stem II. A plurality of nucleotides making up the second flanking region are then covalently-linked to the 5' terminus of the second catalytic core region. This is also accomplished by linking the 3' end of one nucleotide to the 5' end of the catalytic core region, followed by similar linkage of the 3' end of another nucleotide to the 5' end of the bound nucleotide, and so on.

Another aspect of the invention is a ribozyme analog prepared according to the method described above.

The invention also provides a therapeutic formulation including a ribozyme analog of the invention in a physiologically acceptable carrier. In some embodiments, the formulation further includes a facilitator oligonucleotide.

Still another aspect of the invention is a kit including at least one ribozyme analog of the invention. In some embodiments, the kit further includes a facilitator oligonucleotide. Other kits also contain a physiologically acceptable carrier.

Another aspect of the invention is a ribozyme analog which includes a nucleotidic stem-loop II region, first and second flanking regions, and first and second catalytic core regions, the first of which includes a rigid molecular linker. The nucleotide stem-loop II region has a 3' terminus and a 5' terminus and comprises a plurality of 3' to 5' covalently-linked, self-hybridizing nucleotides. The first and second catalytic core regions are each made up of a plurality of 3' to 5' covalently-linked nucleotides, and each core region has a 3' terminus and a 5' terminus. The rigid molecular linker in the first catalytic core region replaces a non-conserved nucleotide and is covalently linked to two of the nucleotides in the region.

The 3' terminus of the first catalytic core region is covalently linked to the 5' terminus of the stem-loop II region, and the 5' terminus of the second catalytic core region being covalently linked to the 3' terminus of the stem-loop II region. To the 5' end of the first catalytic core region is covalently linked a first flanking region, and to the 3' end of the second catalytic core region is covalently linked a second flanking region. The first and second flanking regions each include a plurality of 3' to 5' covalently-linked nucleotides, and each flanking region has a 3' terminus and a 5' terminus, at least a portion of the first flanking region being complementary to a first target region of a substrate RNA molecule, and at least a portion of the second flanking region being complementary to a second target region of the substrate RNA molecule.

In some embodiments of the invention, both the stem-loop II region and at least one of the catalytic core regions contains a rigid molecular linker.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

The patent and scientific literature referred to herein establishes the knowledge that is available to those with skill in the art. The issued U.S. patent, allowed patent applications, and articles cited herein are hereby incorporated by reference.

Figure 1:
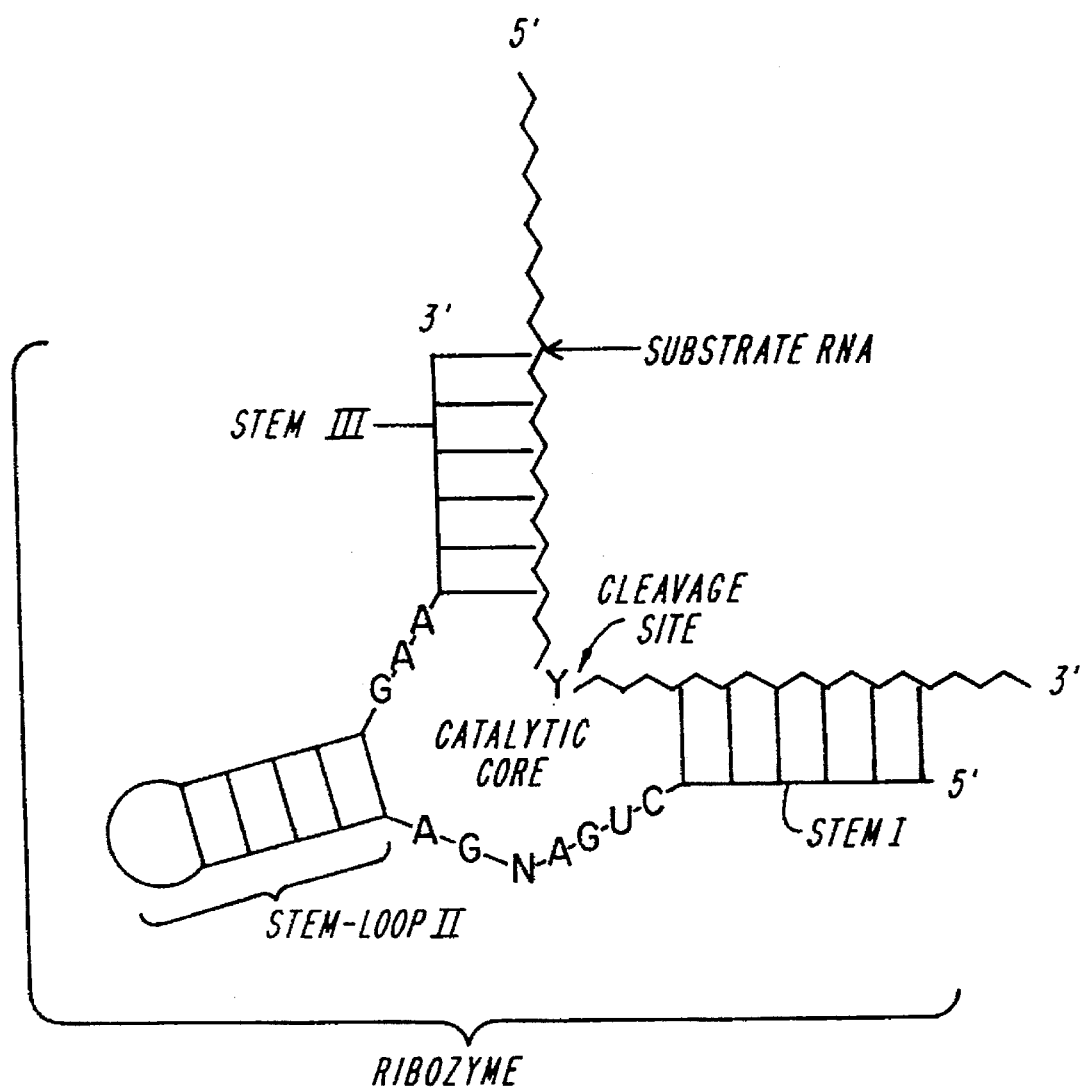
FIG. 1 is a diagrammatic representation of a consensus hammerhead ribozyme hybridized with a substrate RNA, wherein the conserved ribonucleotides (C,U,G,A,G,A,G,A, A) and the non-conserved nucleotide (N) are in the catalytic core of the ribozyme, and wherein cleavage occurs on the 3' side of nucleotide (Y) in the substrate RNA.
Figure 2A:
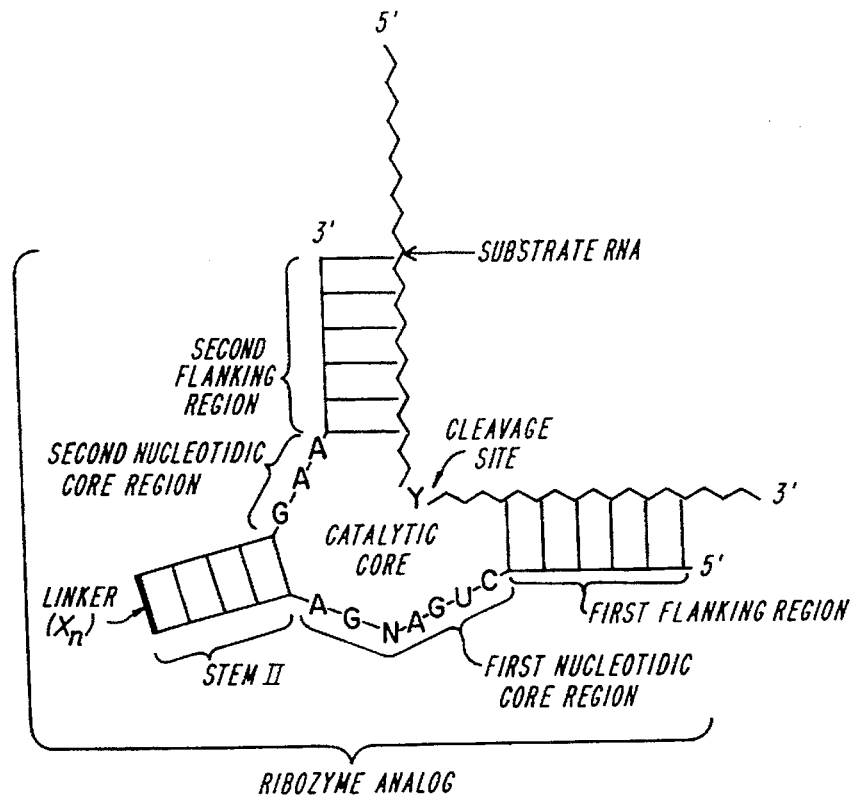
FIG. 2A is a diagrammatic representation of one embodiment of a ribozyme analog of the invention hybridized with a substrate RNA, wherein "$X_n$" refers to non-nucleotidic molecule(s) within the linker.
Figure 2B:
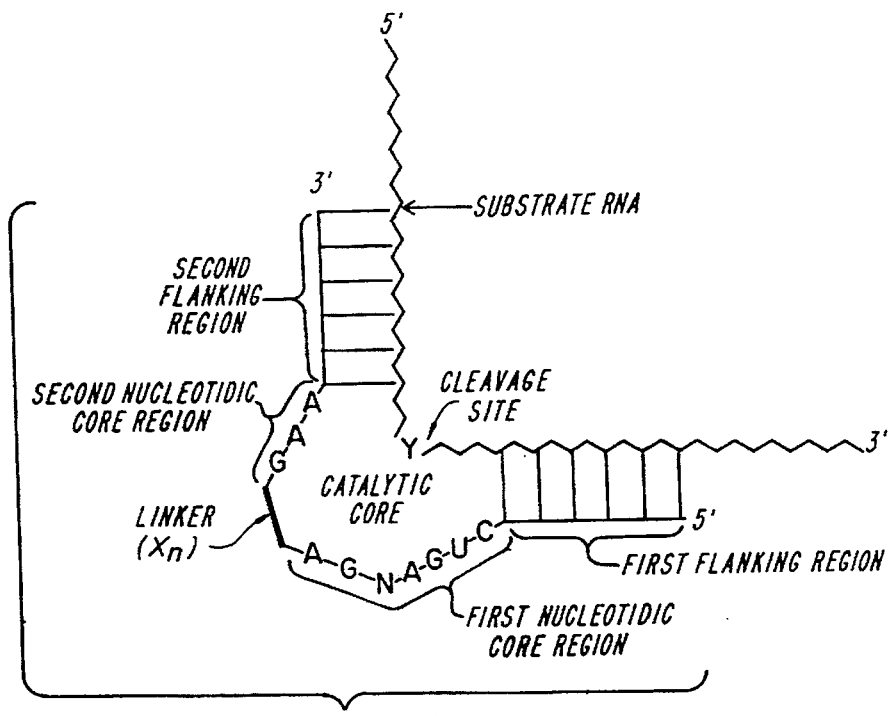
FIG. 2B is a diagrammatic representation of another embodiment of a ribozyme analog of the invention hybridized with a substrate RNA, wherein "$X_n$" refers to non-nucleotidic molecule(s) within the linker.
Figure 2C:
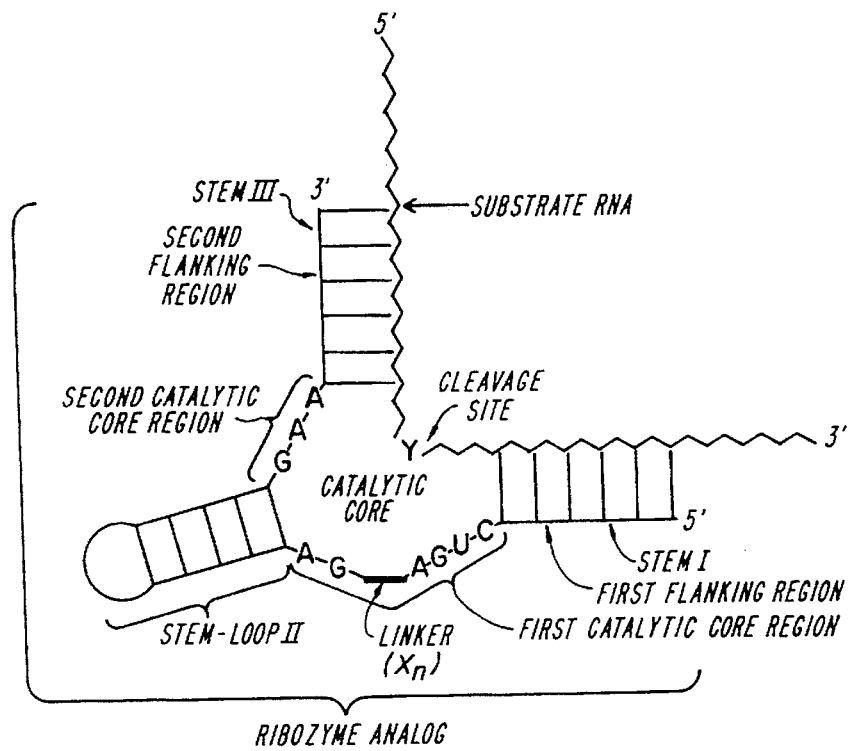
FIG. 2C is a diagrammatic representation of another embodiment of a ribozyme analog of the invention hybridized with a substrate RNA, wherein "$X_n$" refers to non-nucleotidic molecule(s) within the linker.
Figure 2D:
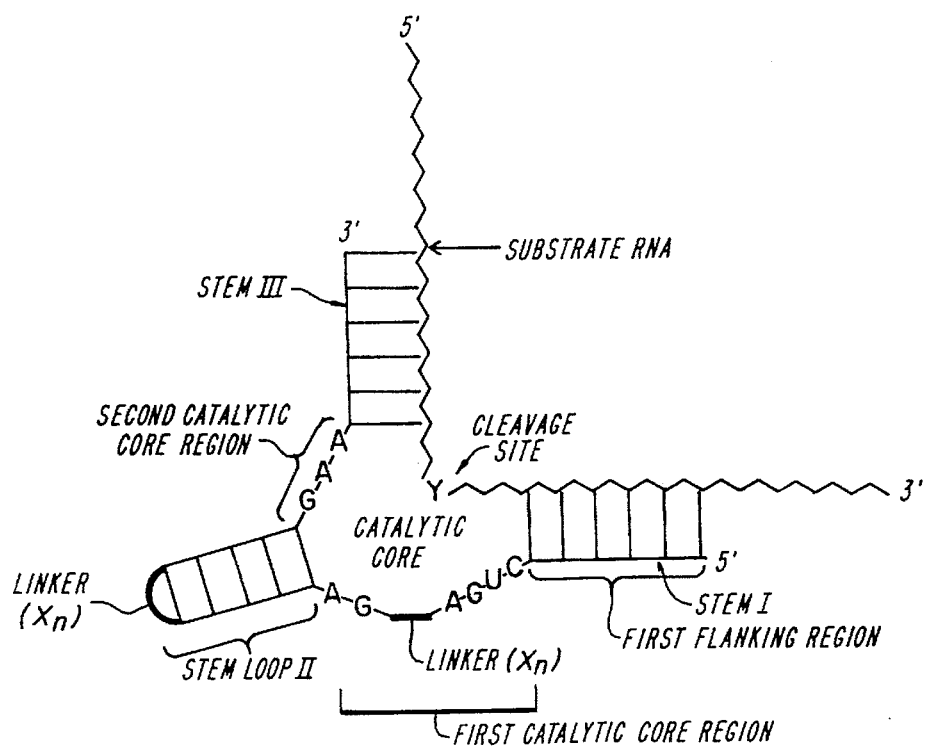
FIG. 2D is a diagrammatic representation of yet another embodiment of a ribozyme analog of the invention hybridized with a substrate RNA, wherein "$X_n$" refers to non-nucleotidic molecule(s) within the linker.

The hammerhead ribozyme, as engineered by Haseloff and Gerlach (*Nature* (1988) 334:585–591), and as depicted in FIG. 1, is composed of a double-stranded stem and loop structure (stem-loop II) connecting two portions of a catalytic core having nine conserved ribonucleotides, and flanked by two regions complementary to the target RNA. The flanking regions enable the ribozyme to bind to the target RNA specifically by forming double stranded stems I and III. Although current belief is that the nucleotide sequence of the ribozymal catalytic core region must be largely conserved in order to maintain the ability of the ribozyme to cleave single-stranded RNA (Koisumi et al. (1991) *Biochem.* 30:5145–5150; Thomson et al. (1993) *Nucleic Acids Res.* 21:5600–5603), it has now been discovered that this cleavage can be accomplished with molecules containing, in their stem-loop or catalytic core regions, rigid molecules other than nucleotides or nucleotide analogs. Furthermore, these non-nucleotidic molecules can be linked together to form a molecular linker useful in antisense oligonucleotides, ribozyme analogs, and other molecules.

These findings have been exploited to develop the present invention, which provides rigid, non-nucleotidic molecular linkers and analogs of hammerhead ribozymes containing such linkers, the latter of which having the ability to endonucleolytically cleave single-stranded RNA and RNA-containing substrates. Thus, ribozyme analogs according to the invention are useful as RNA-specific restriction endonucleases, and as such, in combination with RNA ligases, allow for the preparation of recombinant RNA molecules.

The ribozyme analogs of the invention are structurally distinct from a consensus hammerhead ribozyme in that the stem-loop II, or stem-loop II and/or at least one non-conserved catalytic core region of the ribozyme, has been partially or entirely replaced with a rigid molecular linker that contains neither nucleotides nor nucleotide analogs (see FIGS. 2A–2D). The linker contains at least one rigid non-nucleotidic molecule or "unit" which may be a cyclohexane diol, steroid, lupene diol, or isosorbide, or a combination thereof when the linker consists of more than one molecule. Representative cyclohexane diol, isosorbide, steroid, and lupene diol units are shown in FIGS. 3A–3D, respectively. The rigidity of the molecule(s) making up the linker aids in maintaining the catalytic activity of the ribozyme analog.

The molecular linker may be prepared from various commercially available (e.g., from the Alrich Chemical Co., Milwaukee, Wis.) non-nucleotidic units such as cyclohexane diols, lupene diols, steroids such as β-estradiol, and isosorbide. The precursor molecule is then derivatized in the same way as nucleotides are derivatized for automated synthesis (e.g., dimethoxytritylation and phosphitylation). Alternatively, the non-nucleotidic molecule is synthesized from more basic starting components using methodologies known in the art or by new protocols, such as those as described in the exemplification below.

Figure 4:
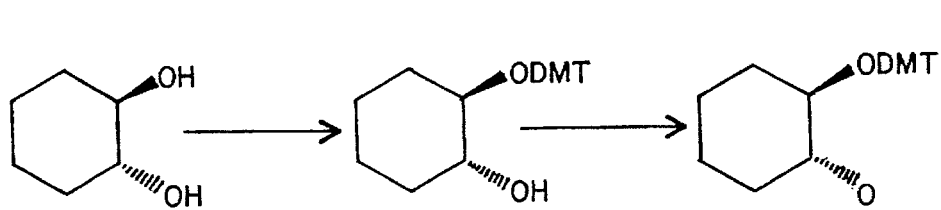
FIG. 4 is a diagrammatic representation of the preparation of a cyclohexane diol unit useful in the molecular linker of the invention.
Figure 4:
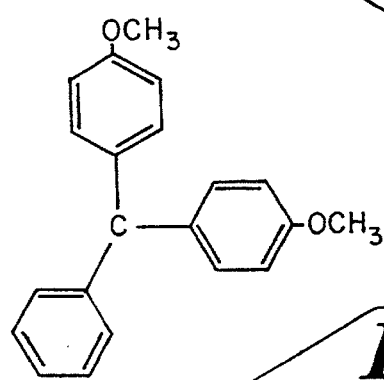

For example, the cyclohexane diol unit trans-1-O-(4,4'-dimethoxytrityl)-2-O-[β-cyanethoxy (N,N-diiopropylamino)] phosphino-1,2-cyclohexanediol (FIG. 3A) can be prepared from trans-1-O-dimethoxytrityl-1,2-cyclohexanediol which itself is prepared from a trans-1,2-cyclohexane diol by treatment with dimethoxytrityl chloride and dimethylaminopyridine. This synthesis is depicted in FIG. 4. The precursor so prepared is dried by evaporation of tetrahydrofuran (THF), treated with β-cyanoethyoxy-N,N-diisopropylaminochlorophosphine and diisopropyl ethylamine (DIPEA) in THF, and purified by chromatography on a silica gel column.

Figure 3A:
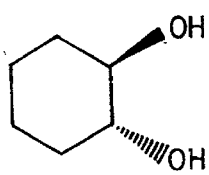
FIG. 3A is a diagrammatic representation of a representative cyclohexane diol unit useful in the molecular linker of the invention.
Figure 3B:
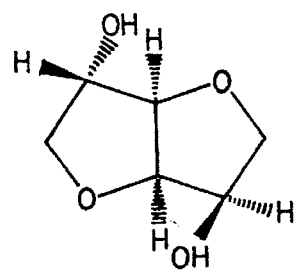
FIG. 3B is a diagrammatic representation of a representative isosorbide useful in the molecular linker of the invention.
Figure 3C:
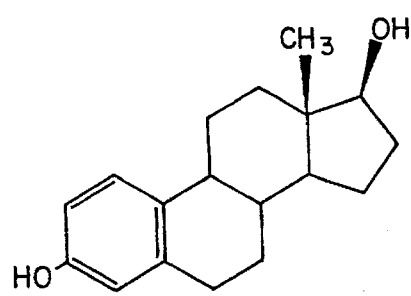
FIG. 3C is a diagrammatic representation of a steroid useful in the molecular linker of the invention.
Figure 3D:
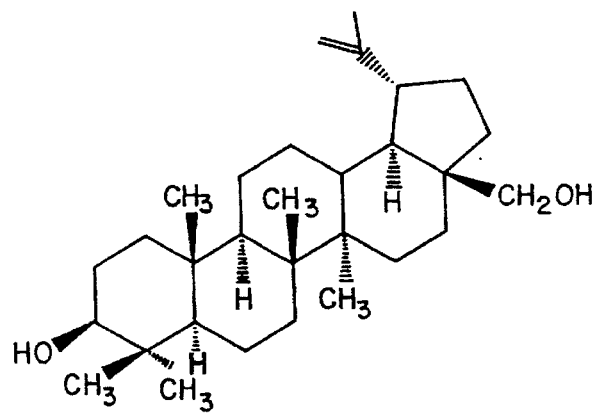
FIG. 3D is a diagrammatic representation of a representative lupene diol useful in the molecular linker of the invention.

Other examples of cyclohexane diols that can be prepared and used in the linker include but are not limited to cis-1,2-cyclohexanediol, cis- and trans-1,3 cyclohexanediol, and cis- and trans-1,4 -cyclohexanediol. A representative useful isosorbide (or bis fused tertrahydrofuran) that can be prepared is 2-O-(4,4-dimethoxytrityl)-5-O-[β-cyanoethoxy(N,N-diiosopropylamino)]phosphino-1,4:3,6-dianhydro-D-glucitol (FIG. 3B). A nonlimiting example of a useful lupene diol is 28-O-(4,4'-dimethoxytrityl)-3-O-(β-cyanoethoxy-N,N-diisopropylaminophosphino)-betulin (FIG. 3D). The molecular linker may be prepared from a number or combination of non-nucleotidic units by covalently linking the individual units together, one by one, in the same way that internucleotide linkages are formed, using well known H-phosphonate, phosphoramidite, or other methods performed manually or by an automated synthesizer.

For example, linker may be prepared via the procedure outlined by Ma (*Biochemistry* (1993) 32:1751–1758) using nucleotide or linker molecule-bound control pore glass solid phase supports. For ribozyme analogs containing at least one ribonucleoside, the deprotection and purification protocol of Ogilvie (ibid.) can be used. To prepare ribozyme analogs not containing ribonucleotides or ribonucleotide analogs, the deprotection and standard purification method(s) of Atkinson et al. (in *Oligonucleotide synthesis: A Practical Approach* (Gait, ed.) IRL Press, Ltd. (Oxford) 1984, pp. 35–81) can be used. However, in some ribozyme analogs one non-nucleotidic unit is sufficient as a linker, as for example when the unit is a lupene diol.

The molecular linker may be covalently attached at one end to the 3' terminus of the first nucleotidic core region, and at its other end, to the 5' terminus of the second nucleotidic core region. The 5' terminus of the first nucleotidic core region is covalently linked to the 3' terminus of the first flanking region, and the 3' terminus of the nucleotidic core region is covalently linked to the 5' terminus of the second flanking region. Each flanking region is composed of at least four contiguous, covalently-linked nucleotides and/or nucleotide analogs.

In addition, each flanking region contains nucleotide sequences which are complementary to, and hybridizable with, target regions on the RNA substrate to be cleaved. The target regions complementary to the flanking regions may be contiguous or separated by one or several nucleotides, depending on the position of the cleavage site.

Flanking regions of the ribozyme analogs or antisense oligonucleotide of the invention are composed of deoxyribonucleotides, analogs of deoxyribonucleotides, ribonucleotides, analogs of ribonucleotides, or a combination thereof, with the 5' end of one nucleotide or nucleotide analog and the 3' end of another nucleotide or nucleotide analog being covalently linked. These flanking regions are at least four nucleotides in length, but are preferably six to fifty nucleotides long, with flanking regions of six to fifteen nucleotides being the most common.

The flanking regions and other nucleotidic regions of the ribozyme analog can be prepared by the art-recognized methods such as phosphoramidate or H-phosphonate chemistry which can be carried out manually or by an automated synthesizer using standard H-phosphonate chemistry as described in U.S. Pat. No. 5,149,789, or using standard phosphoramidite chemistry (see, e.g., Beaucage (*Meth. Mol. Biol.* (1993) 20:33–61); Damha et al. (in *Protocol for Oligonucleotides and Analogs; Synthesis and Properties* (Agrawal, ed.) (1993) Humana Press, Totowa, N.J., pp. 81–114); or Uhlmann et al. (*Chem. Rev.* (1990) 90:534–583).

The flanking regions and other nucleotidic regions of the ribozyme analog may also be modified in a number of ways for protection against nuclease digestion, without compromising the ability of the ribozyme analog to hybridize to substrate RNAs. For example, the nucleotides of the flanking regions and other nucleotidic portions of the ribozyme analog may be covalently linked by other than phosphodiester internucleotide linkages between the 5' end of one nucleotide and the 3' end of another nucleotide, in which the 3' phosphate has been replaced with any number of chemical groups. Examples of such chemical groups include alkylphosphonates, phosphorothioates, phosphorodithioates, alkylphosphonothioates, phosphoramidates, carbamates, acetamidate, carboxymethyl esters, carbonates, and phosphate esters.

Other modifications include those which are internal or at the end(s) of the nucleotidic core or flanking region(s) and include additions to the internucleoside phosphate linkages, such as cholesteryl or diamine compounds with varying numbers of carbon residues between the amino groups and terminal ribose, deoxyribose, and phosphate modifications. Examples of such modified flanking regions include nucleotide sequences having a modified base and/or sugar such as arabinose instead of ribose, or a 3', 5'-substituted nucleoside having a sugar which, at both its 3' and 5' positions is attached to a chemical group other than oxygen or phosphate. Other modified nucleotide sequences are capped with a nuclease resistance-conferring bulky substituent or self-hybridized region at their 3' and/or 5' end(s), or have a substitution in one nonbridging oxygen per nucleotide. Such modifications can be at some or all of the internucleoside linkages, as well as at either or both ends of the oligonucleotide and/or in the interior of the molecule.

The preparation of these modified oligonucleotides is well known in the art (reviewed in Agrawal et al. (1992) *Trends Biotechnol.* 10:152–158; in Goodchild (1990) *Bioconjugate Chem.* 2:165–187); Zon in *Protocols for Oligonucleotides and Analogs* (Agrawal, ed.) Humana Press, Totawa, N.J. (1994) Vol. 20, pp. 165–189). For example, nucleotides can be covalently linked using art-recognized techniques such as phosphoramidite, H-phosphonate, or methylphosphonamidite chemistry.

The 3' terminus of the first flanking region and the 5' terminus of the second flanking region are covalently attached to the catalytic core by any of the methods described above. In some embodiments, the first and/or second flanking region comprises at least one ribonucleotide, such as adenine, at its 5' terminus, which is covalently linked to the 3' terminus of the second nucleotidic core region of the catalytic core.

The structural characteristics of some representative ribozyme analogs of the invention illustrated schematically shown in FIGS. 2A–2D are summarized below in TABLE 1. "Flanking region" refers to the number of nucleotides in each of the first and second flanking regions, and "linker size" refers to the number of non-nucleotidic units in the linker.

TABLE 1

| Ribozyme Analog | Flanking Region (nucleotides) | BPs in Stem II | Linker Size (units) | SEQ ID NO: |
|---|---|---|---|---|
| TL1-75A | 10 | 4 | 4° | 1 |
| TL1-86A | 10 | 0 | 4⁺ | 2 |
| TL1-128A | 6 | 1 | 4° | 3 |
| TL1-130A | 6 | 2 | 4° | 4 |
| TL1-132A | 6 | 3 | 4° | 5 |
| TL1-134A | 6 | 4 | 2° | 6 |
| TL1-140 | 4 | 0 | 1⁺ | 7 |
| TL1-142 | 4 | 2 | 1° | 8 |
| TL1-144 | 4 | 4 | 1° | 9 |
| TL1-146 | 6 | 1 | 6° | 10 |
| TL1-148 | 6 | 2 | 6° | 11 |
| TL1-150 | 6 | 4 | 6° | 12 |
| TL1-160 | 6 | 4 | 1* | 18 |
| R45 | 6 | 5 | 1*, 2° | 19 |

° linker in stem-loop II
\* linker in catalytic core
⁺ linker replacing stem-loop II Using the methods described herein, representative ribozyme analogs TL1-75A (SEQ ID NO:1) TL1-86A (SEQ ID NO:2), and R45 (SEQ ID NO:19) were synthesized and tested for their nucleolytic activity using a single-stranded substrate RNA as follows:

The experiments were conducted simultaneously at pH 8, 9, and 10 in a buffer containing 20 mM magnesium chloride. Magnesium imparts endonucleolytic cleavage activity to a ribozyme. RZMZ-1 (SEQ ID NO:13), a ribozyme with known catalytic activity, was used as a positive control, and substrate RNA (SEQ ID NO:14) in the presence of magnesium was used as a negative control. Based on concentrations of stock solutions determined by UV analysis, samples of ribozyme analogs TL1-75A (SEQ ID NO:1) and TL1-86A (SEQ ID NO:2) were aliquoted into tubes and evaporated. Then, substrate RNA (SEQ ID NO:14), previously incubated at 37° C. for 10 minutes radiolabelled internally using [$\alpha$-$^{32}$P]ATP was taken up in a magnesium-containing buffer and added to the various ribozyme analog samples. The reaction mixtures were incubated at 37° C. for one hour and then subjected to PAGE. The cleavage products in the gels were then analyzed by autoradiography.

Figure 5:
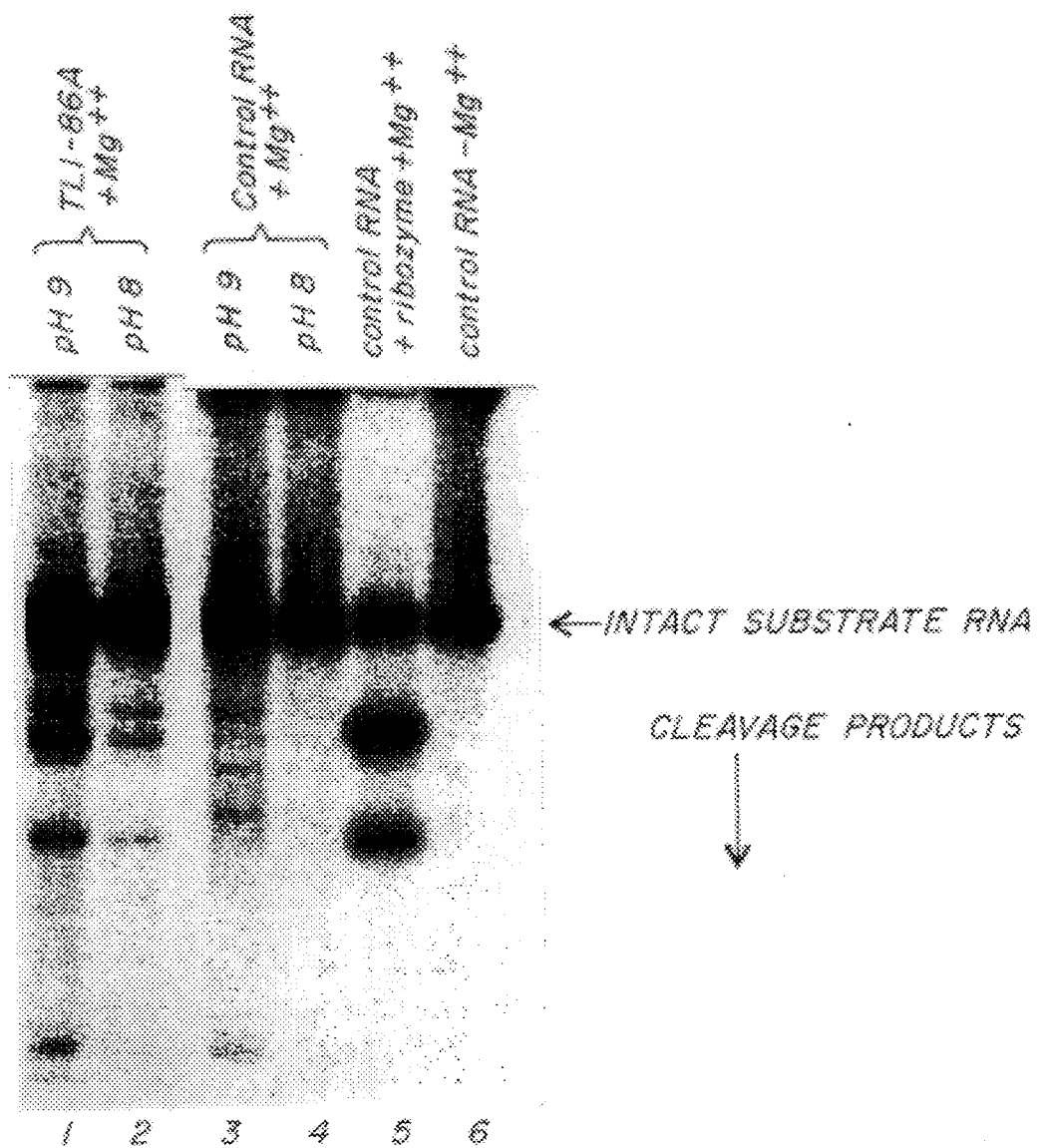
FIG. 5 is a phosphor imager-generated autoradiogram of a polyacrylamide gel through which were run the cleavage products of ribozyme analog TL1-86A-treated $^{32}$P-labelled substrate RNA and ribozyme (control)-treated substrate RNA at pH's 8 and 9 and untreated substrate RNA and ribozyme RZMZ-1 (controls)
Figure 6:
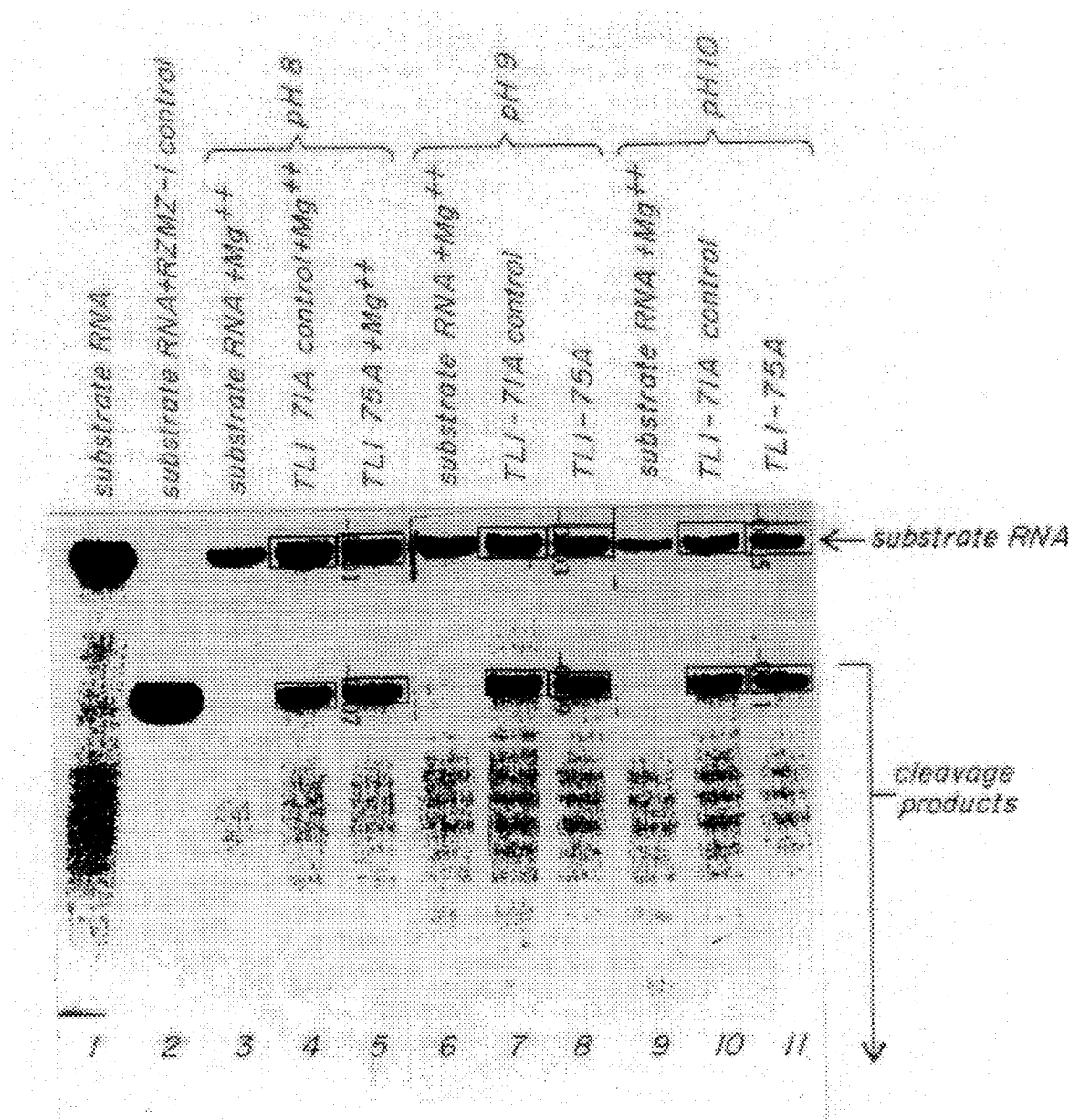
FIG. 6 is a phosphor imager-generated autoradiogram of a polyacrylamide gel through which were run the cleavage products of ribozyme control TL1-71A-treated $^{32}$P-labelled substrate RNA at pH's 8–10, of ribozyme analog TL1-75A-treated substrate RNA at pH's 8–10, of ribozyme control (RZMZ-1), and untreated substrate RNA control.

The results of representative assays are shown in FIGS. 5 and 6. In these gels the substrate RNA samples that had been incubated with the ribozyme analogs of the invention had been partially broken down into lower molecular weight, faster migrating cleavage products. These results demonstrate that the ribozyme analogs tested have endonucleolytic activity at all pH's tested.

Figure 7A:
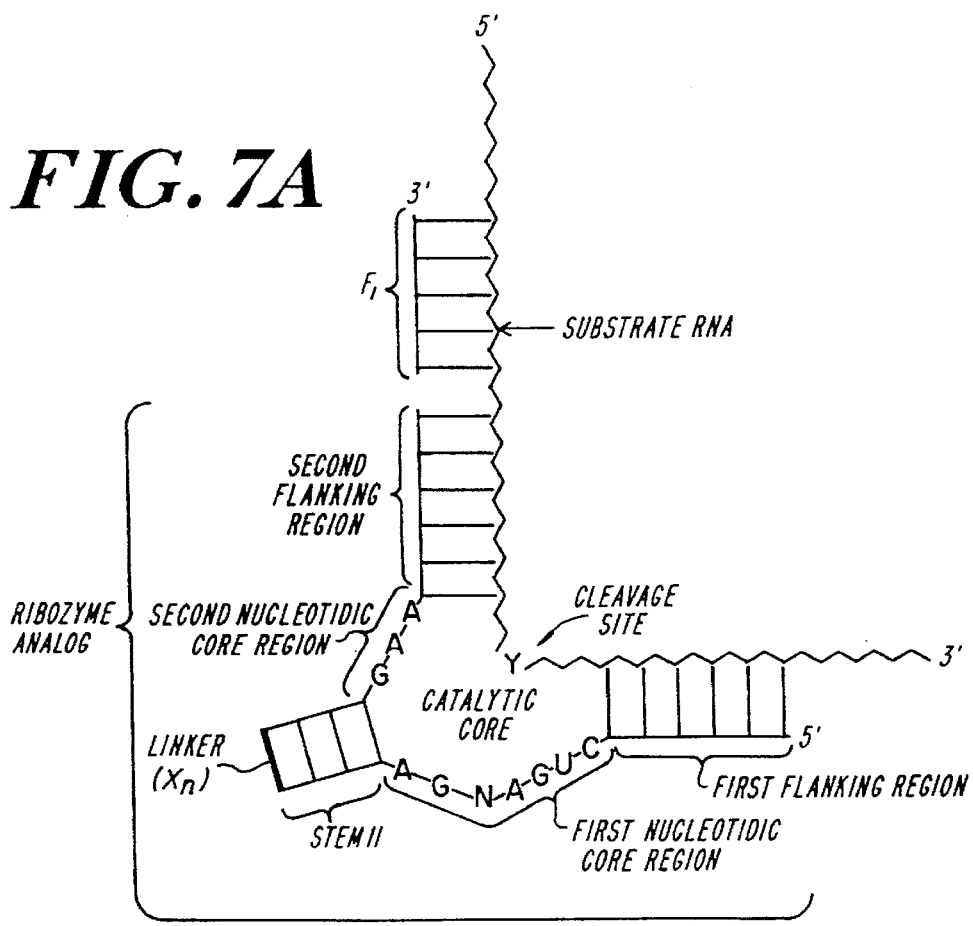
FIG. 7A is a schematic representation of one embodiment of a ribozyme analog of the invention and a facilitator oligonucleotide (F1) hybridized to a substrate RNA.
Figure 7B:
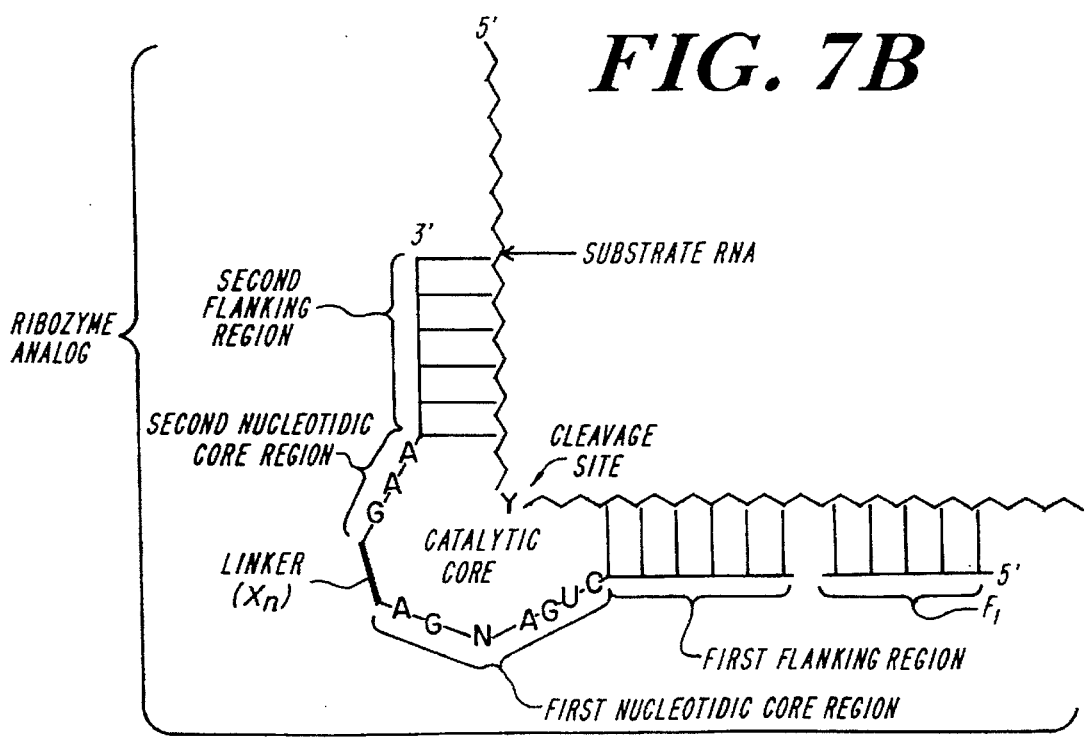
FIG. 7B is a schematic representation of another embodiment of a ribozyme analog of the invention and a facilitator oligonucleotide (F1) hybridized to a substrate RNA.

The cleavage abilities of the ribozyme analogs of the invention may be enhanced by introducing a facilitator oligonucleotide into the system which hybridizes adjacent to the ribozyme analog. Such a facilitator oligonucleotide may be selected to bind to a target sequence on the substrate RNA contiguous with the RNA substrate sequence to which a flanking region binds at the 5' or the 3' side of the ribozyme analog. The catalytic complex formed by the substrate RNA, ribozyme analog, and facilitator oligonucleotide is depicted in FIGS. 7A and 7B. In some situations, a combination of two facilitator oligonucleotides may be employed, where one facilitator is hybridized to the substrate RNA directly adjacent the nucleotide sequence hybridized to the first (5') flanking sequence of the ribozyme analog, and the other facilitator is hybridized to the substrate RNA directly adjacent the nucleotide sequence hybridized to the second (3') flanking sequence of the ribozyme analog. Alternatively, a plurality of facilitators may be employed to enhance ribozyme analog activity. For example, in a system employing three facilitators, two facilitators can bind contiguously to the RNA substrate sequence complementary to first (5') flanking sequence, while a single additional facilitator can bind contiguously to the RNA substrate sequence complementary to the second (3') flanking region. A variety of other combinations are also possible.

In addition, facilitator oligonucleotides may have a nucleotide sequence complementary to regions of the RNA substrate that are not immediately contiguous with the substrate sequences complementary to the ribozyme analog flanking sequences. For example, the facilitator may be synthesized such that, when the ribozyme analog and facilitator oligonucleotide are bound to the substrate RNA, a small gap of from one to about five oligonucleotides exists between the ribozyme analog and the facilitator oligonucleotide. Usually, the gap between the facilitator and the ribozyme analog will be between 0 (zero) and 2 nucleotides. Most often, there will be no nucleotide gap between the facilitator and the ribozyme analog.

The facilitator oligonucleotides of the present invention typically have between about 5 and 50 nucleotides. More preferred facilitator oligonucleotides comprise between about 5 and 15 deoxyribonucleotides. Particularly preferred facilitators according to the invention comprise about 13 nucleotides. Selection of a facilitator of a specific length is related to the length of the ribozyme analog flanking sequences. In addition, some facilitator deoxynucleotides may have a sequence of nucleotides, a portion of which is complementary to the RNA substrate sequence, and a portion of which that is not complementary to the substrate RNA sequence.

Facilitator oligonucleotides can be synthesized on automated DNA synthesizers or manually from DNA templates. They may be synthesized and subsequently modified to include moieties which will influence the rate of substrate cleavage by the ribozyme analog, increase uptake by cells, or increase resistance to degradation. For example, by increasing the number of bases of the substrate RNA bound near the cleavage site, facilitators permit use of faster acting ribozyme analogs with shorter flanking sequences. In viral applications, facilitators might be of dual benefit in also directing cleavage of the viral RNA by endogenous ribonuclease H.

Figure 9:
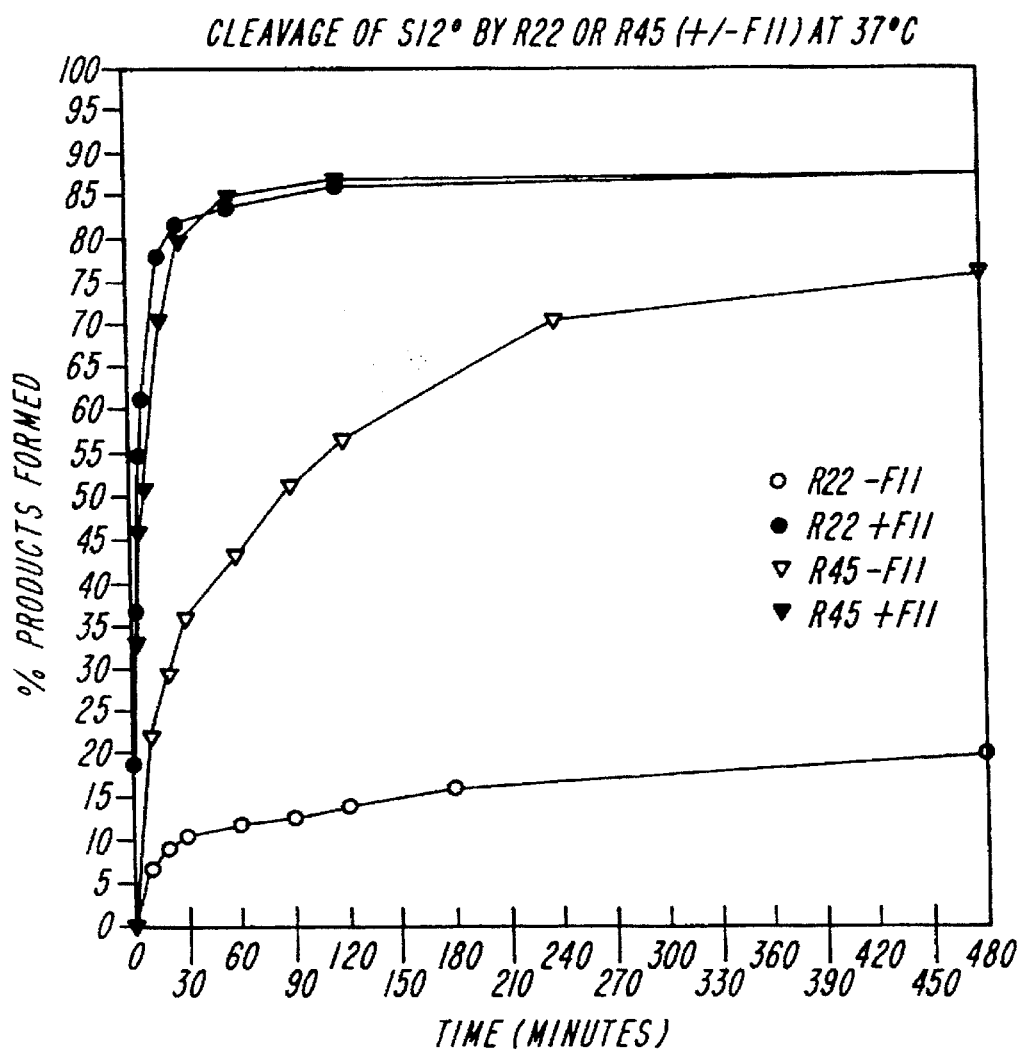
FIG. 9 is a graphic representation of the results of a digestion experiment wherein ribozyme analog R45 and control ribozyme R22 were incubated with $^{32}$P-labelled substrate RNA in the presence or absence of facilitator oligonucleotide F1, and the resulting cleavage products quantitated by PAGE, autoradiography, and scanning densitometry.

To further demonstrate the catalytic capabilities of other ribozyme analogs of the invention and ability of a facilitator oligonucleotide to enhance these capabilities, the following study was performed. Ribozyme analog R45 (SEQ ID NO:19) and control ribozyme R22 (SEQ ID NO:20) were incubated with substrate RNA in the absence and presence of a facilitator oligonucleotide (F1). R45 and R22 are both RNA containing molecules whose flanking regions are linked via phosphorothioate internucleotide linkages. The results shown in FIGS. 9A and 9B demonstrate that with a facilitator, the ribozyme analog R45 (SEQ ID NO:19) is as catalytic as the ribozyme control R22 (SEQ ID NO:20).

To determine the effect of the presence of a facilitator molecule and of reduced flanking sequence length on ribozyme analog activity, various ribozyme analogs (TL1-128A (SEQ ID NO:3); TL1-130A (SEQ ID NO:4), TL1-132A (SEQ ID NO:5), and TL1-134A (SEQ ID NO:6) each with 6 nucleotides in each flanking region, were incubated with substrate RNA (S2) (SEQ ID NO:14) and magnesium, or with substrate RNA and facilitator oligonucleotide (SEQ ID NO:16) in the presence of magnesium, at 37° C. The control ribozyme $R_5$ (SEQ ID NO:15) was treated in the identical fashion. Aliquots were removed from the reaction mixtures tubes after 10 minutes to serve as unincubated ribozyme analog controls. After one hour, the reaction mixtures were placed on ice. An aliquot of an RNA substrate+facilitator stock solution also was taken as an unincubated RNA control. The resulting cleavage products were analyzed by polyacrylamide gel electrophoresis (PAGE).

Figure 8:
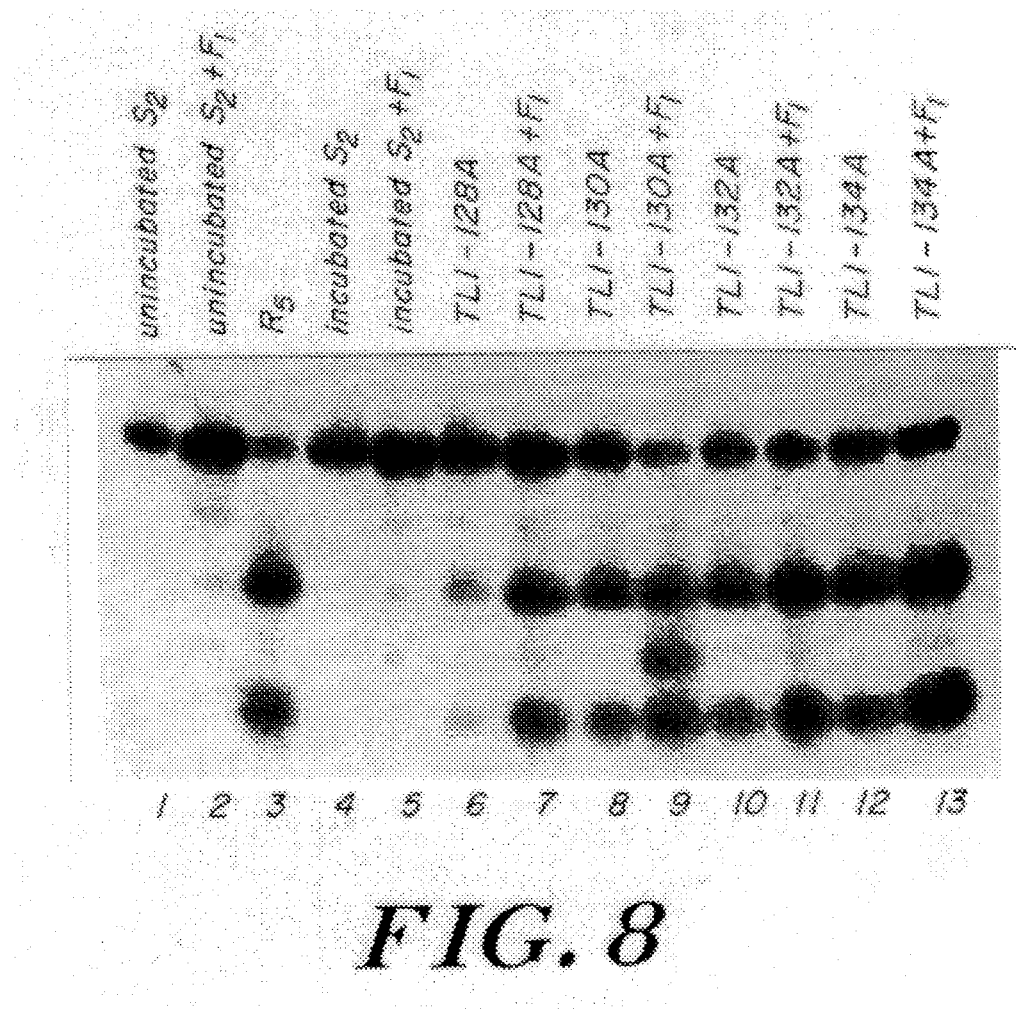
FIG. 8 is a phosphor imager-generated autoradiogram of a polyacrylamide gel through which were run the cleavage products of ribozyme analogs TL1-128A or TL1-134A-treated $^{32}$P-labelled substrate RNA at 45° C. in the presence or absence of a facilitator oligonucleotide (F1) and a ribozyme-treated or untreated substrate RNA in the presence or absence of the facilitator oligonucleotide (F1) at 37° C. (controls)

The results, shown in FIG. 8, demonstrate that substrate RNA samples that had been incubated with the ribozyme analogs of the invention had been partially broken down into lower molecular weight, faster migrating cleavage products by specific cleavage at the same site as in the control ribozyme. Greater cleavage occurred when a facilitator oligonucleotide was added to the incubation mixture (lanes 7, 9, 11, and 13), further indicating the ability of the ribozyme analogs of the invention to cleave RNA.

The ribozyme analogs of the invention can be provided for any method of use in the form of a kit including a container of a ribozyme analog of the invention, of mixtures of different ribozyme analogs, or of ribozyme analog(s) and facilitator oligonucleotide(s), and/or a container of facilitator oligonucleotide(s) alone. The amount of ribozyme analog or of ribozyme analog and facilitator oligonucleotide in the container may be sufficient for one therapeutic dose or assay. Alternatively, the amounts of the kit constituents may be concentrated such that only small aliquots need be sampled at one time from the container when used, for example, to cleave RNA molecules in vitro. The kits must preserve the ribozyme analog(s) and facilitator oligonucleotides in active form.

The present invention also provides therapeutic formulations containing a ribozyme analog, or a ribozyme analog and a facilitator oligonucleotide(s) useful for treatment. These therapeutic formulations must be administered to individuals in a manner capable of delivering the ribozyme analog and/or ribozyme analog and facilitator oligonucleotide initially into the body and subsequently into any number of target cells.

One mode of administration is via a therapeutic formulation which contains at least one ribozyme analog, as described above, along with a physiologically acceptable carrier. Some therapeutic formulations contain more than one type of ribozyme analog of the invention, and some include facilitator oligonucleotides.

As used herein, a "physiologically acceptable carrier" includes any and all solvents, dispersion media, coatings, antibacterial and antifungal agents, isotonic and absorption-delaying agents, and agents which improve oligonucleotide uptake, and the like. The use of such media and agents for pharmaceutically active substances is well known in the art. Except insofar as any conventional medium or agent is incompatible with the active ingredient, its use in the therapeutic compositions is contemplated. Supplementary active ingredients can also be incorporated into the compositions.

The pharmaceutical forms suitable for injectable use include sterile aqueous solutions or dispersions and sterile powders for the extemporaneous preparation of sterile injectable solutions or dispersions. In all cases the form must be sterile. It must be stable under the conditions of manufacture and storage and may be preserved against the contaminating action of microorganisms, such as bacteria and fungi. The carrier can be a solvent or dispersion medium. The prevention of the action of microorganisms can be brought about by various antibacterial and antifungal agents. Prolonged absorption of the injectable therapeutic agents can be brought about by the use of the compositions of agents delaying absorption.

The therapeutic formulations of the invention may be administered parenterally, orally, by inhalation of spray, or rectally in dosage unit formulations containing conventional non-toxic pharmaceutically acceptable carriers, adjuvants and vehicles. The term "parenteral" as used herein includes subcutaneous injections, intravenous, intramuscular, intrasternal injection or infusion techniques.

The amount of active ribozyme analog that may be combined with the carrier materials to produce a single dosage form will vary depending upon the host treated and the particular mode of administration. It will be understood that the specific dose level for any particular patient will depend upon a variety of factors including the activity of the specific composition employed, the age, body weight, general health, sex, diet, time of administration, route of administration, severity of the particular disease undergoing therapy.

The ribozyme analogs of the invention, themselves, or in a therapeutic formulation may be administered for any purpose known to those with skill in the art that a ribozyme or antisense oligonucleotide may be used. For example, cells infected with a virus may be treated with a ribozyme analog having flanking sequences complementary to nucleotide sequences of a particular mRNA corresponding to a viral gene in order to hinder the expression of that gene. Similarly, ribozyme analogs may be administered to stop the expression of cancer-related genes, or of any gene which is being overexpressed.

The following examples illustrate the preferred modes of making and practicing the present invention, but are not meant to limit the scope of the invention since alternative methods may be utilized to obtain similar results.

EXAMPLES

1. Preparation of Rigid Molecular Linker

In order to prepare a trans-1-O-(4,4'-dimethoxytrityl)-2-O-[β-cyanoethoxy-(N,N-diisopropylamino)] phosphino-1,2-cyclohexanediol-containing linker, a precursor form of the unit, trans-1-O-dimethoxytrityl-1,2-cyclohexanediol is needed. This precursor is prepared as follows:

1.16 g (10 mmol) of trans-1,2 cyclohexanediol was dissolved in 50 ml of anhydrous pyridine. This solution was evaporated to dryness and the procedure was repeated twice to remove any water present. The flask was then sealed and flushed with argon. Next, a solution was made by dissolving 3.4 g (10.1 mmol) of dimethoxytrityl chloride and 20 mg of dimethylaminopyridine in 50 ml of anhydrous pyridine. This solution was added to the first mixture, via syringe, dropwise over 30 minutes. This reaction mixture was then stirred at room temperature for 18 hours.

An aliquot of the solution was analyzed by thin layer chromatography (TLC) in hexane:ethyl acetate:triethylamine (50:20:1), yielding a spot corresponding to the desired product and faint spots corresponding to dialkylated product and dimethoxytritanol. The solvent was removed in vacuo and the residue taken up in 125 ml of dichloromethane. This was washed with 5% sodium bicarbonate and twice with brine. The solvent was removed and the resulting gum taken up in hexanes:ethyl acetate:triethylamine and applied to a silica gel column containing the same solvent. Fractions containing the desired product were combined and evaporated to give 1.0 g (2.38 mmol) 25% yield of product.

Material prepared by this method was used in the next step by dissolving 3.72 g (8.9 mmol) of dimethoxytritryl cyclohexanediol (precursor) in 40 ml of anhydrous tetrahydrofuran (THF), and evaporating to dryness. The procedure was repeated twice. Next, the residue was taken up in 40 ml of THF, to which was added 6.2 ml of diisopropylethylamine (35.4 mmol). The flask was sealed and flushed with argon. Then, 4.21 g (17.8 mmol) of [β-cyanoethyoxy(N,N-diisopropylamino)]chlorophosphine in 25 ml of dry THF was added, dropwise with stirring at room temperature, over 30 minutes. A white precipitate formed. 45 minutes after the final addition, TLC in hexanes:ethyl acetate:triethylamine, 50:20:1, showed the reaction to be complete. One milliliter of water was added and the reaction mixture stirred for 15 minutes. Solvent was evaporated and the residue taken up in 250 ml of ethyl acetate. The organic layer was washed once with 75 ml of 5% sodium bicarbonate and once with 75 ml of brine. It was then dried over sodium sulfate, filtered, and evaporated to a small volume. The residue was applied to a silica gel column and the desired product eluted in hexanes:ethylacetate:triethylamine, 50:10:1. The fractions containing the desired product were pooled and evaporated to give 3.68 g (5.94 mmol) 67% yield of desired product.

2. Chemical Synthesis of Ribozyme Analog

The nucleotidic flanking regions containing unmodified (phosphodiester-linked) ribonucleotides, deoxyribonucleotides, or both, were synthesized on an automated DNA synthesizer (Applied BioSystems, Foster City, Calif.) on a 1.0 μmole scale using standard H-phosphonate chemistry as described in U.S. Pat. No. 5,149,789, or using standard phosphoramidite chemistry as described by Beaucage (*Meth. Mol. Biol.* (1993) 20:33–61) or Uhlmann et al. (*Chem. Rev.* (1990) 90:534–583). Flanking regions with at least one non-phosphodiester internucleotide linkage including a phosphoramidite, methylphosphonate, and/or a 2'-O-methyl substitutions at preselected positions were prepared using the procedures described in Agrawal and Goodchild (*Tetrahedron Lett.* (1987) 28:3539–3542); Agrawal et al. (*Proc. Natl. Acad. Sci.* (*USA*) (1988) 85:7079–7083); and/or Uhlmann et al. (*Chem. Rev.* (1990) 90:534–583). Flanking regions having at least one phosphorodithioate, carbamate, phosphate ester, 2'-O-methyl, alkylphosphonate, phosphoramidate, alkylphosphonothioate, carbonate, acetamidate, and/or carboxymethyl ester nucleotide analog are prepared as described by any art recognized methods in (reviewed in *Protocols For Oligonucleotides and Analogs* (*Meth. Mol. Bio.* (Agrawal, ed.) Humana Press, Totowa, N.J., Vol. 20, 1993); Agrawal et al. (1992) *Trends Biotechnol.* 10:152–158; Goodchild (1990) *Bioconjugate Chem.* 1:165–187; and Uhlmann et al. (*Chem. Rev.* (1990) 90:534–583).

Ribonucleotides were incorporated into the core region by the standard method of Usman et al. (1987) *J. Amer. Chem. Soc.* 109:7845–7854. Non-nucleotidic phosphoramidites were incorporated into oligonucleotides using the same standard protocols as for nucleotides.

The product was cleaved from the support and deprotected by heating in 1 ml of concentrated aqueous ammonia:ethanol (3:1, v/v) in a sealed tube at 55° C. for 17 hours. Following centrifugation at 14,000 rpm for 3 minutes, the CPG support was washed twice with 400 μl of water, and the combined supernatant and washings were divided in half and placed in separate tubes and evaporated to dryness. One tube was stored at −20° C. for later use; the other was treated with 400 μl of tetra-N-butylammonium fluoride (TBAF) 1.0M in THF (Aldrich Chemical Co., Milwaukee, Wis.) for 16 hours at room temperature.

3. Purification of Ribozyme Analogs

To the oligonucleotide sample was added 400 μl of 50 mM Tris, pH 8 and 800 μl of 95% formamide containing 0.05% Orange G dye (Sigma, St. Louis, Mo.). The sample was then loaded onto a 15% polyacrylamide gel containing 8M urea. Electrophoresis was carried out at 25 watts constant power until the dye reaches the bottom of the gel. The desired band was identified by shadowing with a UV lamp against a fluorescent background. This band was cut out of the gel, crushed with a pestle, and extracted with 12 ml of 0.5M ammonium acetate for 12 hours. The mixture was centrifuged and the combined supernatant passed through a $C_{18}$ Sep-Pak cartridge (Waters, Marlborough, Mass.) at a rate of 2 ml per minute. The cartridge was washed with water and the ribozyme analog eluted with 4 ml 50% aqueous acetonitrile at 2 ml per minute. The eluate was evaporated and the residue taken up in 200 μl of 0.3M NaCl. Next, 600 μl of absolute ethanol was added and the mixture stored at −20° C. for 16 hours. The mixture was centrifuged at 14,000 rpm for 20 minutes and the supernatant decanted. The pellet was redissolved in 200 μl of 0.1M NaCl and precipitated with 600 μl of absolute ethanol. The suspension was placed on dry ice for 30 minutes and centrifuged. The supernatant was removed and the pellet dissolved in 400 μl of water and stored at −20° C. until used.

4. Preparation of Facilitator Oligonucleotide

Facilitator oligonucleotides which contain unmodified (phosphodiester-linked) deoxyribonucleotides were synthesized on an automated DNA synthesizer (Applied BioSystems, Foster City, Calif.) as described in EXAMPLE 2 above.

5. Cleavage Activity Assay

Substrate RNA radiolabelled internally using [$\alpha$-$^{32}$P] ATP (Amersham, Arlington Heights, Ill.) was prepared as described by Goodchild et al. (*Arch. Biochem. Biophys.* (1991) 284:386–391) using T7 RNA polymerase (New England Biolabs, Beverly, Mass.) and a chemically synthesized single stranded template with a double stranded promoter (Milligan et al. (1987) *Nucleic Acids Res.* 15:8783–8798).

The experiments were conducted simultaneously at pH 8, 9, and 10 in 50 mM Tris buffer containing 20 mM magnesium chloride. The final ribozyme analog concentration in all cases was 50 µM and that of substrate RNA was 4 nM. Final reaction volumes were 5 µl. An active control ribozyme (SEQ ID NO:13) was used as a positive control, and substrate RNA (SEQ ID NO:14) alone in 20 mM magnesium chloride, 50 mM Tris was used as a negative control. Based on concentrations of stock solutions determined by UV analysis, ribozyme analog samples TL1-75A (SEQ ID NO:1) and TL1-86A (SEQ ID NO:2) were concentrated by evaporation. The substrate RNA was taken up in Tris-magnesium buffer and added to the evaporated ribozyme analog samples. The mixtures were then incubated at 37° C. for one hour. Next, 5 µl 95% formamide dye containing 0.05% Orange G dye (Sigma, St. Louis, Mo.) was added and the reaction mixtures loaded directly onto a preheated (45° C.), 15% polyacrylamide gel containing 8M urea. The gels were analyzed by a phosphorimager (Molecular Dynamics, Sunnyvale, Calif.) and by autoradiography.

6. The Effects of Reduced Flanking Sequence Length and Facilitator Presence on Ribozyme Analog Cleavage Activity The following procedure was used to examine the effects of reduced flanking sequence length and facilitator presence on the cleavage activity of ribozyme analogs TL1-128A (SEQ ID NO:3), TL1-130A (SEQ ID NO:4), TL1-132A (SEQ ID NO:5), and TL1-134A (SEQ ID NO:6). Based on concentrations of stock solutions of ribozyme analogs obtained on work up, 25 picomoles of each of the ribozyme analogs were taken up and concentrated by evaporation. Substrate RNA (S2) (SEQ ID NO:14) was prepared according to the procedure of Goodchild et al. (*Arch. Biochem. Biophys.* (1991) 284:386–391) based on that of Milligan et al. (*Nucleic Acids Res.* (1987) 15:8783–8798). Two stock solutions of substrate were prepared; one containing 0.5 µM substrate RNA and the other containing 0.5 µM substrate RNA plus 1.0 µM facilitator oligonucleotide, F1 (SEQ ID NO:16). Both stock solutions contained 50 mM Tris, pH 7.4, and 20 mM magnesium chloride. All ribozyme samples contained 20 mM magnesium chloride and 50 mM Tris, pH 7.4. Control ribozyme R5 (SEQ ID NO:17) was treated in the identical fashion. Final reaction volumes were 10 µl.

All tubes were heated to 37° C. for 10 minutes. Five microliter aliquots were removed from the substrate and substrate+facilitator stock solutions. Five microliters of 95% formamide dye containing 0.05% Orange G dye (Sigma, St. Louis, Mo.) are added, and these mixtures, which served as unincubated controls, were placed on ice. Reactions were initiated by adding 5 µl of substrate stock to each of the tubes containing ribozyme analog or ribozyme control R5 (SEQ ID NO:17). Reactions employing facilitator were initiated in a similar manner. 5 µl were taken as an incubated control. Then, 5 µl of substrate+facilitator were taken as an unincubated RNA control, and 5 µl added to duplicate tubes containing the ribozyme analog. All tubes except those containing the unincubated controls were heated at 37° C. for one hour.

7. Electrophoretic Analysis of Cleavage Products

Twenty microliters of orange formamide dye was added to each reaction tube described in EXAMPLE 5 above and the contents loaded onto a 15% polyacrylamide gel containing 8M urea, is preheated to 45° C. Electrophoresis was carried out at 25 watts constant power until the dye is off the bottom of the gel. The results from phosphor-imaging are shown in FIGS. 5–8.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A hammerhead ribozyme analog comprising:

(a) a stem region having a 3' terminus and a 5' terminus and comprising a rigid, non-nucleotidic molecular linker composed of molecules selected from the group consisting of cyclohexane diols, steroid diols, lupene diols, isosorbide, and combinations thereof, and a nucleotidic stem;

(b) a first nucleotidic core region comprising a plurality of 5' to 3' covalently-linked nucleotides and having a 5' terminus and a 3' terminus;

(c) a second nucleotidic core region comprising a plurality of 5' to 3' covalently linked nucleotides and having a 5' terminus and a 3' terminus;

(d) a nucleotidic first flanking region complementary to a first target region located at a 3' position of a cleavage site on a substrate RNA molecule; and (e) a nucleotidic second flanking region complementary to a second target region located at a 5' position of the cleavage site, wherein:

(i) the linker provides a structure corresponding to a loop portion of a hammerhead ribozyme stem-loop II region;

(ii) the 3' terminus of the first nucleotidic core region is covalently linked to the 5' terminus of the stem region and the 5' terminus of the first nucleotidic core region is covalently linked to the first flanking region; and (iii) the 5' terminus of the second nucleotidic core region is covalently linked to the 3' terminus of the stem region and the 3' terminus of the second nucleotidic core region is covalently linked to the second flanking region.

2. The ribozyme analog of claim 1 wherein the linker comprises from two to twenty rigid non-nucleotide molecules.

3. The ribozyme analog of claim 2 wherein the non-nucleotide molecules are linked to each other and to the stem region via a linkage selected from the group consisting of a phosphodiester, an alkylphosphonate, a phosphoramidate, a phosphorothioate, a phosphate ester, a phosphorodithioate, an alkylphosphonothioate, a carbamate, an acetamideate, a carbonate, a carboxymethyl ester, and combinations thereof.

4. The ribozyme analog of claim 2 wherein the linker comprises four contiguous, covalently-linked cyclohexane diol molecules.

5. The ribozyme analog of claim 1 wherein the linker comprises a cyclohexane diol selected from the group consisting of trans-1,2-cyclohexane diol, cis-1,2-cyclohexane diol, trans-1,3-cyclohexane diol, cis-1,3-cyclohexane diol, trans-1,4-cyclohexane diol, cis-1,4-cyclohexane diol, and combinations thereof.

6. The ribozyme analog of claim 1, wherein the nucleosides of said first and second flanking regions and of said first and second nucleotidic core regions are linked by an internucleoside linkage selected from the group consisting of a phosphodiester, an alkylphosphonate, a phosphorothioate, a phosphorodithioate, an alkylphosphonothioate, a phosphoramidate, a phosphate ester, a carbamate, a carbonate, an acetamidate, a carboxymethyl ester, and a combination thereof.

7. The ribozyme analog of claim 1 wherein the nucleotides of said first and second flanking regions and of said first and second nucleotidic core regions are selected from the group consisting of ribonucleotides, analogs of ribonucleotides, deoxyribonucleotides, analogs of deoxyribonucleotides, and combinations thereof.

8. The ribozyme analog of claim 7 wherein the ribonucleotide and deoxyribonucleotide analogs are selected from the group consisting of alkylphosphonates, phosphorothioates, phosphorodithioates, alkylphosphonothioates, phosphoramidates, phosphate esters, carbamates, carbonates, acetamidates, carboxymethyl esters, and combinations thereof.

9. The ribozyme analog of claim 7 wherein at least one of the ribonucleotide analogs is a 2'-O-methyl analog.

10. The ribozyme analog of claim 1 wherein the first and second flanking regions each comprise four nucleotides, nucleotide analogs, or combinations thereof.

11. A kit comprising the ribozyme analog of claim 1.

12. The kit of claim 11 further comprising a facilitator oligonucleotide.

13. A hammerhead ribozyme analog comprising:

(a) a rigid, non-nucleotidic molecular linker composed of molecules selected from the group consisting of cyclohexane dials, steroid dials, lupene dials, isosorbide, and combinations thereof, having a first hydroxyl and a second hydroxyl;

(b) a first nucleotidic core region comprising a plurality of 5' to 3' covalently-linked nucleotides and having a 5' terminus and a 3' terminus;

(c) a second nucleotidic core region comprising a plurality of 5' to 3' covalently linked nucleotides and having a 5' terminus and a 3' terminus;

(d) a nucleotidic first flanking region complementary to a first target region located at a 3' position of a cleavage site on a substrate RNA molecule; and (e) a nucleotidic second flanking region complementary to a second target region located at a 5' position of the cleavage site, wherein:

(i) the linker provides a structure corresponding to a stem-loop II region of a hammerhead ribozyme;

(ii) the 3' terminus of the first nucleotidic core region is covalently linked to the first hydroxyl and the 5' terminus of the first nucleotidic core region covalently linked to the first flanking region; and (iii) the 5' terminus of the second nucleotidic core region is covalently linked to the second hydroxyl and the 3' terminus of the second nucleotidic core region is covalently linked to the second flanking region.

14. The ribozyme analog of claim 13 wherein the linker comprises from two to twenty rigid non-nucleotide molecules.

15. The ribozyme analog of claim 14 wherein the non-nucleotide molecules are linked to each other and to the termini of the catalytic core regions via a linkage selected from the group consisting of a phosphodiester, an alkylphosphonate, a phosphoramidate, a phosphorothioate, a phosphorodithioate, a phosphate ester, an alkylphosphonothioate, a carbamate, a carbonate, a carboxymethyl ester, an acetamidate, and combinations thereof.

16. The ribozyme analog of claim 13 wherein the linker comprises four contiguous, covalently-linked cyclohexane diol molecules.

17. The ribozyme analog of claim 13 wherein the linker comprises a cyclohexane diol selected from the group consisting of trans-1,2-cyclohexane diol, cis-1,2-cyclohexane diol, trans-1,3-cyclohexane diol, cis-1,3-cyclohexane diol, trans-1,4-cyclohexane diol, cis-1,4-cyclohexane diol, and combinations thereof.

18. The ribozyme analog of claim 13, wherein the nucleosides of said first and second flanking regions and of said catalytic core are linked by an internucleoside linkage selected from the group consisting of a phosphodiester, an alkylphosphonate, a phosphorothioate, a phosphorodithioate, an alkylphosphonothioate, a phosphoramidate, a phosphate ester, a carbamate, a carbonate, an acetamidate, a carboxymethyl ester, and a combination thereof.

19. The ribozyme analog of claim 13 wherein the nucleotides of said first and second flanking regions and of said catalytic core are selected from the group consisting of ribonucleotides, analogs of ribonucleotides, deoxyribonucleotides, analogs of deoxyribonucleotides, and combinations thereof.

20. The ribozyme analog of claim 19 wherein the ribonucleotide and deoxyribonucleotide analogs are selected from the group consisting of alkylphosphonates, phosphorothioates, phosphorodithioates, alkylphosphonothioates, phosphoramidates, phosphate esters, carbamates, carbonates, acetamidates, carboxymethyl esters, and combinations thereof.

21. The ribozyme analog of claim 19 wherein at least one of the ribonucleotide analogs is a 2'-O-methyl analog.

22. The ribozyme analog of claim 13 wherein the first and second flanking regions each comprise four nucleotides, nucleotide analogs, or combinations thereof.

23. A kit comprising the ribozyme analog of claim 13.

24. The kit of claim 23 further comprising a facilitator oligonucleotide.

25. A hammerhead ribozyme analog comprising:

(a) a nucleotidic stem-loop II region having a 3' terminus and a 5' terminus;

(b) a first nucleotidic core region having a 5' terminus and a 3' terminus and comprising a plurality of 3' to 5' covalently-linked conserved and non-conserved nucleotides and at least one rigid, non-nucleotidic molecule selected from the group consisting of cyclohexane diols, steroid diols, lupene diols, isosorbide, replacing a non-conserved nucleotide, thereby forming a rigid molecular linker;

(c) a second nucleotidic core region comprising a plurality of 5' to 3' covalently linked nucleotides and having a 5' terminus and a 3' terminus;

(d) a first flanking region complementary to a first target region located at a 3' position of a cleavage site on a substrate RNA molecule; and (e) a second flanking region complementary to a second target region located at a 5' position of the cleavage site; wherein:

(i) the 3' terminus of the first nucleotidic core region is covalently linked to the 5' terminus of the stem-loop II region and the 5' terminus of the first nucleotidic core region is covalently linked to the first flanking region; and (ii) the 5' terminus of the second nucleotidic core region is covalently linked to the 3' terminus of the stem-loop II region and the 3' terminus of the second nucleotidic core region is covalently linked to the second flanking region.

26. A kit comprising the ribozyme analog of claim 25.

27. The kit of claim 26 further comprising a facilitator oligonucleotide.

28. The ribozyme analog of claim 25 wherein the stem-loop II region comprises a nucleotidic stem structure and a rigid, non-nucleotidic loop structure.

29. A rigid molecular linker for linking nucleic acid monomers of an oligonucleotide comprising from two to twenty covalently linked non-nucleotidic molecules selected from the group consisting of cyclohexane diols, steroid diols, lupene diols, isosorbide, and combinations thereof.

30. The linker of claim 29 wherein the non-nucleotidic molecules are linked to each other via a linkage selected from the group consisting of a phosphodiester, a phosphoramidate, an alkylphosphonate, a phosphorothioate, an acetamidate, a phosphorodithioate, a phosphate ester, an alkylphosphonothioate, a carbamate, a carbonate, a carboxymethyl ester, and combinations thereof.

31. The linker of claim 29 comprising four contiguous, covalently-linked cyclohexane diol molecules.

32. The linker of claim 30 comprising a cyclohexane diol selected from the group consisting of trans-1,2-cyclohexane diol, cis-1,2-cyclohexane diol, trans-1,3-cyclohexane diol, cis-1,3-cyclohexane diol, trans-1,4-cyclohexane diol, cis-1,4-cyclohexane diol, and combinations thereof.

33. A rigid molecular linker for linking nucleic acid monomers of an oligonucleotide comprising one lupene diol.

34. A method of preparing a rigid molecular linker comprising:

(a) preparing a plurality of trans-1-O-(4,4'-dimethoxytrityl)-2-O-[β-cyanoethoxy-(N,N-diisopropylamino)]phosphino-1,2-cyclohexanediol units;

(b) covalently linking a first trans-1-O-(4,4'-dimethoxytrityl)-2-O-[β-cyanoethoxy-(N,N-diisopropylamino)]phosphino-1,2-cyclohexanediol unit to a second trans-1-O-(4,4'-dimethoxytrityl)-2-O-[β-cyanoethoxy-(N,N-diisopropylamino)]phosphino-1,2-cyclohexanediol unit via a phosphodiester linkage;

(c) covalently linking a third trans-1-O-(4,4'-dimethoxytrityl)-2-O-[β-cyanoethoxy-(N,N-diisopropylamino)]phosphino-1,2-cyclohexanediol unit to the second trans-1-O-(4,4'-dimethoxytrityl)-2-O-[β-cyanoethoxy-(N,N-diisopropylamino)] phosphino-1,2-cyclohexanediol unit;

(d) covalently linking a fourth trans-1-O-(4,4'-dimethoxytrityl)-2-O-[β-cyanoethoxy-(N,N-diisopropylamino)]phosphino-1,2-cyclohexanediol unit to the third trans-1-O-(4,4'-dimethoxytrityl)-2-O-[β-cyanoethoxy-(N,N-diisopropylamino)]phosphino-1,2-cyclohexanediol unit, thereby forming the molecular linker.

35. A molecular linker prepared according to the method of claim 34.

* * * * *